(12) United States Patent
Sampas et al.

(10) Patent No.: US 10,538,796 B2
(45) Date of Patent: Jan. 21, 2020

(54) ON-ARRAY LIGATION ASSEMBLY

(71) Applicant: Agilent Technologies, Inc., Santa Clara, CA (US)

(72) Inventors: Nicholas M Sampas, San Jose, CA (US); Jeffrey R Sampson, San Jose, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 13 days.

(21) Appl. No.: 15/782,648

(22) Filed: Oct. 12, 2017

(65) Prior Publication Data

US 2018/0105853 A1  Apr. 19, 2018

Related U.S. Application Data

(60) Provisional application No. 62/407,748, filed on Oct. 13, 2016.

(51) Int. Cl.
*C12P 19/34* (2006.01)
*C12N 15/10* (2006.01)
*C12N 15/66* (2006.01)

(52) U.S. Cl.
CPC .......... *C12P 19/34* (2013.01); *C12N 15/1006* (2013.01); *C12N 15/66* (2013.01)

(58) Field of Classification Search
None
See application file for complete search history.

(56) References Cited

U.S. PATENT DOCUMENTS

| | | |
|---|---|---|
| 5,948,902 A | 9/1999 | Honkanen et al. |
| 6,171,797 B1 | 1/2001 | Perbost |
| 6,180,351 B1 | 1/2001 | Cattell |
| 6,232,072 B1 | 5/2001 | Fisher |
| 6,242,266 B1 | 6/2001 | Schleifer et al. |
| 6,323,043 B1 | 11/2001 | Caren et al. |
| 2004/0152905 A1 | 8/2004 | Guzaev et al. |
| 2005/0233340 A1 | 10/2005 | Barrett et al. |
| 2007/0259357 A1 | 11/2007 | Brenner |
| 2015/0361422 A1 | 12/2015 | Sampson et al. |

FOREIGN PATENT DOCUMENTS

| | | |
|---|---|---|
| EP | 3000883 A1 | 3/2016 |
| JP | 2012223203 A | 11/2012 |
| WO | 2013028643 A1 | 2/2013 |
| WO | 2014151696 A1 | 9/2014 |
| WO | 2015195257 A1 | 12/2015 |

OTHER PUBLICATIONS

Brenner, et al., "Encoded Combinatorial Chemistry", Proceedings of the National Academy of Sciences; 1992 89(12), 1992, 5381-5383.
Cleary, et al., "Production of Complex Nucleic Acid Libraries using Highly Parallel in situ Oligonucleotide Synthesis", Nature Methods, vol. 1, No. 3, 2004, 241-248.
Ferretti, et al., "Temperature dependence of the joining by T4 DNA ligase of termini produced by type II restriction endonucleases", Nucleic Acids Research; 1981 9(1), 1981, 85-93.
Leproust, et al., "Synthesis of High-quality Libraries of Long (150mer) Oligonucleotides by a Novel Depurination Controlled Process", Nucleic Acids Research, vol. 38, No. 8, 2010, 2522-2540.
Pohl, et al., "Temperature Dependence of the Activity of DNA-Modifying Enzymes: Endonucleases and DNA Ligase", European Journal of Biochemistry;123(1), 1982, 141-152.
Siying, et al., "Error correction in gene synthesis technology", Trends in Biotechnology; 2012 30(3), 2012, 147-154.
Extended European Search Report dated Feb. 13, 2018, Application No. 17196353.1, 7 pages.

*Primary Examiner* — Nancy J Leith

(57) ABSTRACT

Provided herein, among other things, is a method for producing a ligation product on a support. In some embodiments, the method may comprise hybridizing a first double-stranded oligonucleotides and a second double-stranded oligonucleotide to a substrate comprising surface-tethered oligonucleotides and ligating the distal ends of the first and second double-stranded oligonucleotides together, thereby producing a first ligation product that is tethered to the support at both ends.

22 Claims, 14 Drawing Sheets

Specification includes a Sequence Listing.

| Lane | | Input 1 | Input 2 | Meas-Inputs | Product (pmol/L) | Yield | Ratio: Prod/Input | Fraction sampled | Sample Volume (uL) | Quantity in Well (pmol) |
|---|---|---|---|---|---|---|---|---|---|---|
| 1 | Well A 50 C Array_0092 | | | | | | | | | |
| 2 | Well A 60 C | 24,370.4 | - | 12,185.2 | 51,809.2 | 81% | 4.25 | 0.2 | 1 | 0.26 |
| 3 | Well A 70 C | 2,145.0 | - | 1,072.5 | 12,719.7 | 92% | 11.86 | 0.2 | 1 | 0.06 |
| 4 | Brenda613 Set B Tubel Lig Product 1:20 | 1,438.7 | - | 719.4 | 2,976.1 | 81% | 4.14 | | | |
| 5 | Well B 50 C | 15,568.7 | - | 7,784.4 | 7,317.5 | 48% | 0.94 | 0.2 | 1 | 0.04 |
| 6 | Well B 60 C | 14,021.2 | - | 7,010.6 | 30,568.4 | 81% | 4.36 | 0.2 | 1 | 0.15 |
| 7 | Well B 70 C | 5,020.5 | - | 2,510.3 | 12,562.3 | 83% | 5.00 | 0.2 | 1 | 0.06 |
| 8 | Brenda613 Set B Oli-Mix 1:500 | | | | | | | | | |
| 9 | Well C 70 C | 16,207.8 | - | 8,103.9 | 34,300.2 | 81% | 4.20 | 0.2 | 1 | 0.17 |
| 10 | Brenda613 Set B Tubel Lig Product 1:20 | 1,199.7 | - | 599.9 | 2,456.2 | 80% | 4.09 | | | |
| 11 | Well D 70 C | 6,883.3 | 4,405.1 | 5,634.2 | 20,301.5 | 78% | 3.60 | 0.2 | 1 | 0.10 |

FIG. 13

Construct representations by correct paired read counts for EK499 gene

SEQUENCE LISTING

<160> NUMBER OF SEQ ID NOS: 12

<210> SEQ ID NO 1
<211> LENGTH: 80
<212> TYPE: DNA
<213> ORGANISM: Artificial Sequence
<220> FEATURE:
<223> OTHER INFORMATION: Synthetic Construct

<400> SEQUENCE: 1
catgctacgt atcgcagtga ttgcacaacg agatgactca ggcggacctc ttatctgcga    60
tggcatcttg cagggcacga                                                80

<210> SEQ ID NO 2
<211> LENGTH: 50
<212> TYPE: DNA
<213> ORGANISM: Artificial Sequence
<220> FEATURE:
<223> OTHER INFORMATION: Synthetic Construct

<400> SEQUENCE: 2
attagtataa atggcaggta ccectggctt gccgcagggg actggcccat                50

<210> SEQ ID NO 3
<211> LENGTH: 50
<212> TYPE: DNA
<213> ORGANISM: Artificial Sequence
<220> FEATURE:
<223> OTHER INFORMATION: Synthetic Construct

<400> SEQUENCE: 3
ggggtgatgg agccccaacc ggaagcaaga cactttgaac cgggtttcgg                50

<210> SEQ ID NO 4
<211> LENGTH: 80
<212> TYPE: DNA
<213> ORGANISM: Artificial Sequence
<220> FEATURE:
<223> OTHER INFORMATION: Synthetic Construct

<400> SEQUENCE: 4
ctatacgact ctaggcgtgt accatgtggt ccagcgttct tcatcatcgt atctttgatc    60
caagaattaa atttgatcaa                                                80

<210> SEQ ID NO 5
<211> LENGTH: 80
<212> TYPE: DNA
<213> ORGANISM: Artificial Sequence
<220> FEATURE:
<223> OTHER INFORMATION: Synthetic Construct

<400> SEQUENCE: 5
catgctacgt atcgcagtga ttgcacaacg gacgtaatgc tttgtgctgg cgaaatggga    60
gggggaaaag atacgtgtag                                                80

<210> SEQ ID NO 6
<211> LENGTH: 50
<212> TYPE: DNA
<213> ORGANISM: Artificial Sequence
<220> FEATURE:
<223> OTHER INFORMATION: Synthetic Construct

<400> SEQUENCE: 6
tcatctctac acgtatcttt tcccctccc atttcgccag cacaaagcat                 50

```
<210> SEQ ID NO 7
<211> LENGTH: 50
<212> TYPE: DNA
<213> ORGANISM: Artificial Sequence
<220> FEATURE:
<223> OTHER INFORMATION: Synthetic Construct

<400> SEQUENCE: 7
agatgactca ggcggacctc ttatctgcga tggcatcttg cagggcacga          50

<210> SEQ ID NO 8
<211> LENGTH: 80
<212> TYPE: DNA
<213> ORGANISM: Artificial Sequence
<220> FEATURE:
<223> OTHER INFORMATION: Synthetic Construct

<400> SEQUENCE: 8
catgctacgt atcgcagtga ttgcacaacg gacgtaatgc tttgtgctgg cgaaatggga          60
gggggaaaag atacgtgtag          80

<210> SEQ ID NO 9
<211> LENGTH: 60
<212> TYPE: DNA
<213> ORGANISM: Artificial Sequence
<220> FEATURE:
<223> OTHER INFORMATION: Synthetic Construct

<400> SEQUENCE: 9
cgttgtgcaa tcactgcgat acgtagcatg accacatggt acacgcctag agtcgtatag          60

<210> SEQ ID NO 10
<211> LENGTH: 60
<212> TYPE: DNA
<213> ORGANISM: Artificial Sequence
<220> FEATURE:
<223> OTHER INFORMATION: Synthetic Construct

<400> SEQUENCE: 10
accacatggt acacgcctag agtcgtatag cgttgtgcaa tcactgcgat acgtagcatg          60

<210> SEQ ID NO 11
<211> LENGTH: 60
<212> TYPE: DNA
<213> ORGANISM: Artificial Sequence
<220> FEATURE:
<223> OTHER INFORMATION: Synthetic Construct

<400> SEQUENCE: 11
acaggttcag agttctacag tccgacgatc ctggagttca gacgtgtgct cttccgatct          60

<210> SEQ ID NO 12
<211> LENGTH: 60
<212> TYPE: DNA
<213> ORGANISM: Artificial Sequence
<220> FEATURE:
<223> OTHER INFORMATION: Synthetic Construct

<400> SEQUENCE: 12
ctggagttca gacgtgtgct cttccgatct acaggttcag agttctacag tccgacgatc          60
```

ON-ARRAY LIGATION ASSEMBLY

CROSS-REFERENCE TO RELATED APPLICATIONS

This application claims the benefit of U.S. Provisional Patent Application. No. 62/407,748, filed Oct. 13, 2016, which is incorporated by reference herein in its entirety.

BACKGROUND

High-throughput synthesis and assembly of DNA constructs is an integral part of synthetic biology and the bio-engineering cycle which aims to revolutionize how molecular and biological products are de veloped and manufactured. A number of methods for the assembly of synthetic DNA oligonucleotides into longer constructs have been developed over the past several years. Many methods utilize a combination of polymerase or ligase enzymes to join shorter oligonucleotides (e.g., molecules that are 50 to 200 nucleotides in length) to form constructs that are as long as 1,000 to 5,000 base-pairs. These methods are sufficient for the construction of whole genes coding for functional proteins.

any high throughput methods are performed in micro-titer plates$_{using}$ automated robotic systems. While these systems reduce the cost of labor, the reagent costs, including the starting oligonucleotides, are still considerable given the number and the volume of the various reactions required for the assembly.

SUMMARY

This disclosure provides, among other things, a method for producing a ligation product on a support, in some embodiments, the method may comprise hybridizing a first double-stranded oligonucleotides and a second double-stranded oligonucleotide to a substrate comprising surface-tethered oligonucleotides and ligating the surface-distal ends of the first and second double-stranded oligonucleotides together, thereby producing a first ligation product that is tethered to the support at both ends.

BRIEF DESCRIPTION OF THE FIGS

The skilled artisan will understand that the drawings, described below, are for illustration purposes only. The drawings are not intended to limit the scope of the present teachings in any way.

FIG. 1 schematically illustrates some of the general principles of an embodiment of the present method, FIG. 2 schematically illustrates a set of double stranded oligonucleotides that are going to be assembled together and substrate comprising surface-tethered oligonucleotides. In the embodiment shown, the surface-tethered oligonucleotides are in the form of an array.

FIG. 3 schematically illustrates the product of hybridization of the double-stranded oligonucleotides to the substrate (in excess) and washing way any unbound or incomplete double-stranded oligonucleotides.

FIG. 4 schematically illustrates the product of ligation of two double-stranded oligonucleotides on the substrate, to produce a ligation product that is tethered to the support at both ends. In the embodiment shown, one strand of the ligation product is covalently linked to a surface-tethered oligonucleotide, whereas the other strand is tethered to the support by base-pairing with a surface-tethered oligonucleotide.

FIG. 13 shows a table of quantified concentrations and product yields as measured on a BioAnalyzer.

Figure 14:
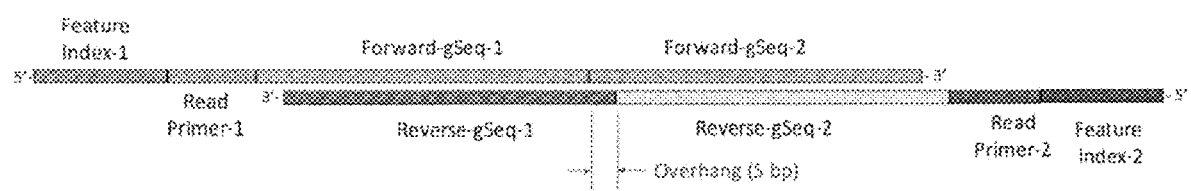

FIG. 14 schematically illustrates the design of each construct in the complex OLS library.

Figure 15:
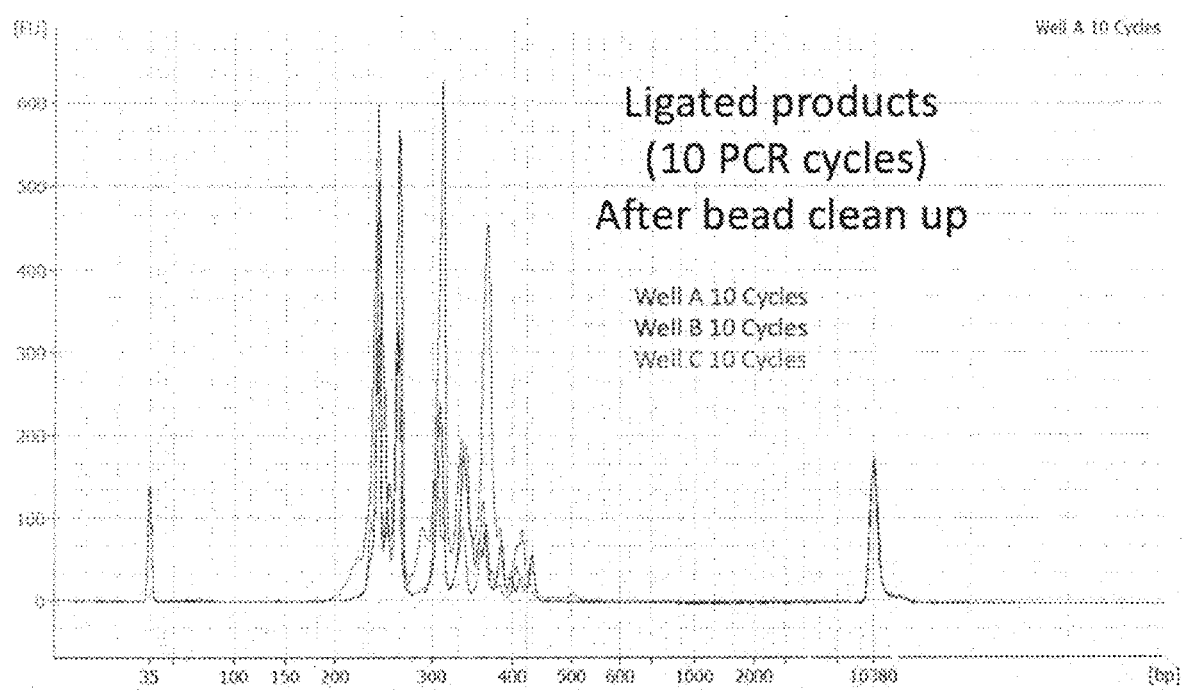

FIG. 15 shows cleaned up PCR amplified complex ligation products.

Figure 16:
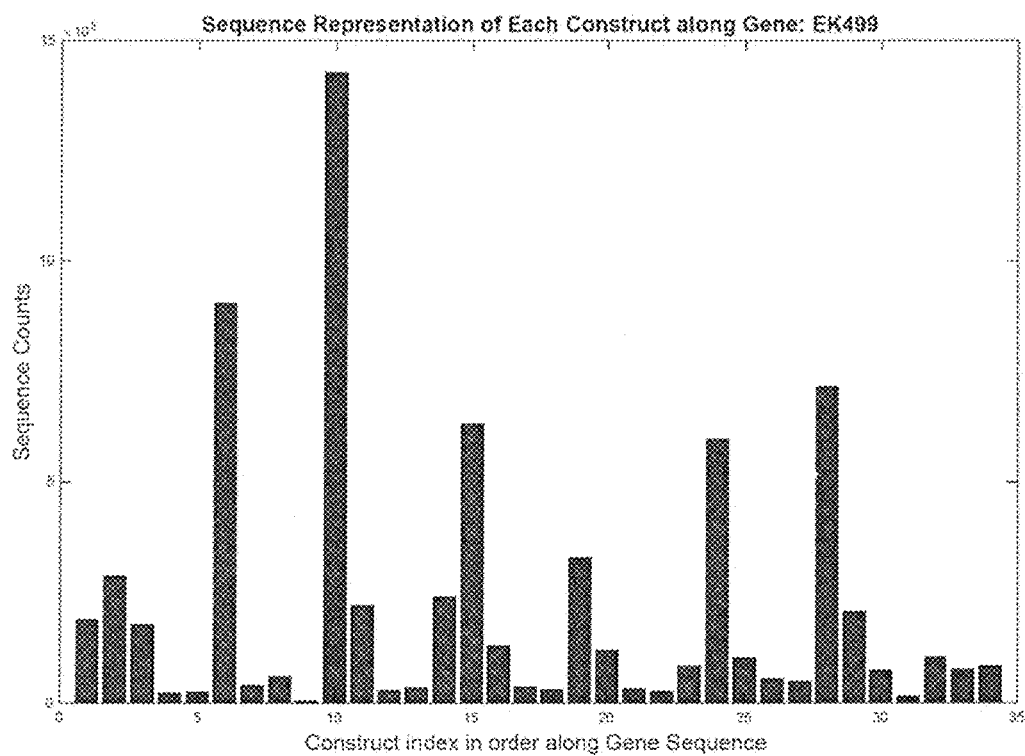

FIG. 16 shows the representations of intended constructs in Example 3.

Figure 17:
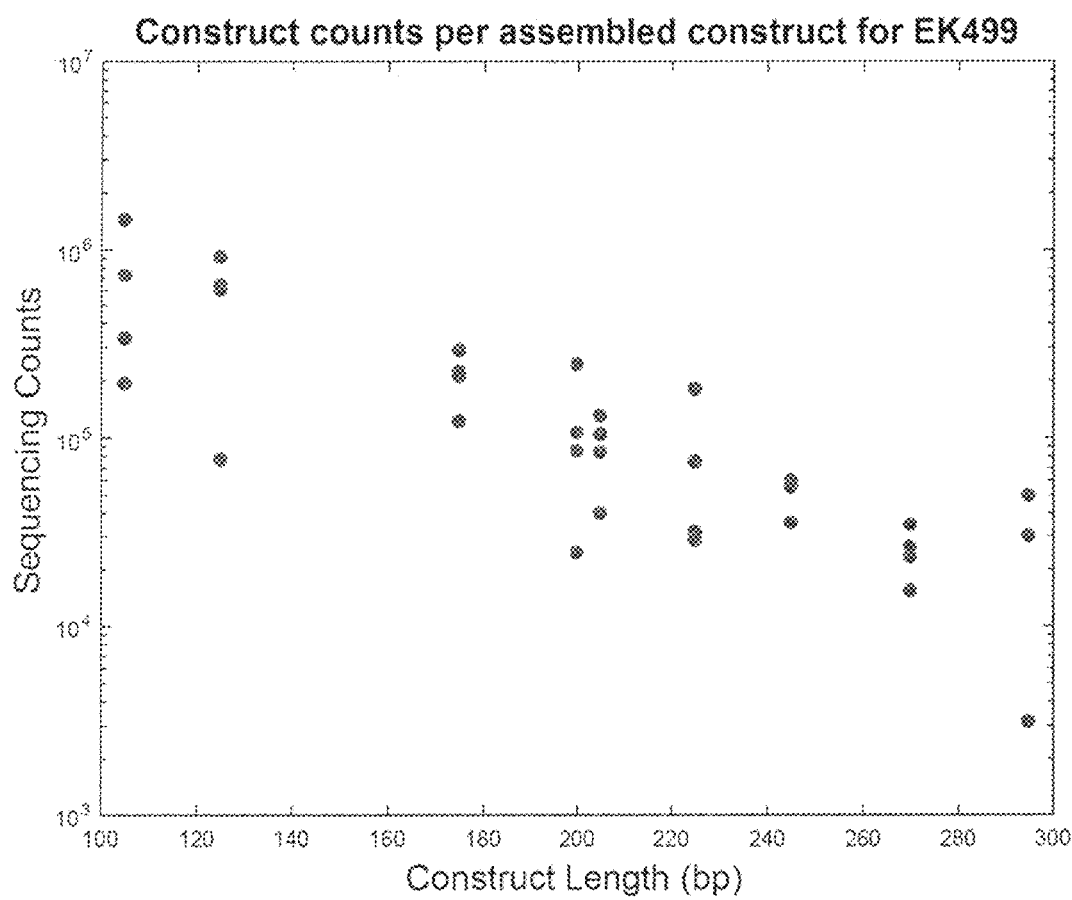

FIG. 17 shows that longer constructs are Substantially less represented than shorter constructs.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely", "only" and the like in connection with the recitation of claim elements, or use of a "negative" limitation.

As used herein, the term "array" is intended to describe a two-dimensional arrangement of addressable regions bearing oligonucleotides associated with that region. The oligonucleotides of an array may be covalently attached to substrate at any point along the nucleic acid chain, but are generally attached at one terminus (e.g. the 3' or 5' terminus).

Any given substrate may carry one, two, four or more arrays disposed on a front surface of the substrate. Depending upon the use, any or all of the arrays may be the same or different from one another and each may contain multiple spots or features. An array may contain at least 10, at least 100, at least 1,000, at least 10,000, at least 100,000, or at least $10^6$ or more features, in an area of less than 20 cm$^2$, e.g., in an area of less than 10 cm$^2$, of less than 5 cm$^2$, or of less than 1 cm$^2$. In some embodiments, features may have widths (that is, diameter, for a round spot) in the range from 1 μm to 1.0 cm, although features outside of these dimensions are envisioned. In some embodiments, a feature may have a width in the range of 3.0 μm to 200 μm, e.g., 5.0 μm to 100 μm or 10 μm to 50 μm. Interfeature areas will typically be present which do not carry any polymeric compound. It will be appreciated though, that the interfeature areas, when present, could be of various sizes and configurations.

Each array may cover an area of less than 100 cm$^2$, e.g., less than 50 cm$^2$, less than 10 cm$^2$ or less than 1 cm$^2$. In some embodiments, the substrate carrying the one or more arrays will be shaped generally as a rectangular or square solid (although other shapes are possible), having a length of more than 4 mm and less than 10 cm, e.g., more than 5 mm and less than 5 cm, and a width of more than 4 mm and less than 10 cm, e.g., more than 5 mm and less than 5 cm.

Arrays can be Fabricated using drop deposition from pulse jets of either polynucleotide precursor units (such as monomers) in the case of in situ fabrication, or the previously obtained polynucleotide. Such methods are described in detail in, for example, U.S. Pat. Nos. 6,242,266, 6,232, 072, 6,130,351, 6,171,797, 6,323,043, U.S. patent application Ser. No. 09/302,898 filed Apr. 30, 1999 by Carers et al., and the references cited therein. These references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature", "spot" or "area" of the array) is at a particular predetermined location (i.e., an "address") on the array. Array features are typically, but need not be, separated by intervening spaces.

The term "nucleotide" is intended to include those moieties that contain not only the known purine and pyrimidine bases, but also other heterocyclic bases that have been modified. Such modifications include methylated purines or pyrimidines, acylated purines or pyrimidines, or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as an inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a multimer of nucleotide of about 2 to 200 nucleotides, up to 500 nucleotides in length. In some embodiments, an oligonucleotide may be in the range of 30 to 300 nucleotides in length. Oligonucleotides may contain ribonucleotide monomers (i.e., may be oligoribonucleotides) and/or deoxyribonucleotide monomers. An oligonucleotide maybe 10 to 20, 21 to 30, 31 to 40, 41 to 50, 51-60, 61 to 70, 71 to 80, 80 to 100, 100 to 150 or 150 to 200 nucleotides in length, for example.

As used herein, the term "pre-defined" is intended to refer to something that is known prior to being made.

As used herein, the term "mixture" is intended to refer to a solution in which the components are interspersed with one another and not spatially separated.

As used herein, the term "aqueous" is intended to refer to a medium in which the solvent comprises water.

As used herein, the terms "sets", "multiple" and "plurality" refer to a population that contains at least 2 members. In certain cases, a plurality may have at least 10, at least 100, at least 1,000, at least 10,000, at least 100,000, at least $10^6$, at least $10^7$, at least $10^8$ or at least $10^9$ or more members.

As used herein, the term "in the solution phase" is intended to refer to a polymeric compound that is in an aqueous environment that is not bound or tethered to a solid substrate. Such a polymeric compound may be dissolved in the aqueous environment.

As used herein, the term "contacting" is intended to mean placing into contact. The term "contacting an array with a solution" is intended to encompass direct contact between an array and solution, e.g., by dipping or misting, as well as depositing a solution on the surface of the substrate by other means.

As used herein, a "mixture of double-stranded oligonucleotides" refers to an aqueous solution that contains a plurality of different double-stranded oligonucleotides dissolved therein. A mixture may comprise at least 50, at least 100, at least 500 at least 1,000, at least 5,000, at least 10,000 or at least 50,000 or more of oligonucleotides. A mixture of oligonucleotides may be made by synthesizing the oligonucleotides in situ, i.e., synthesizing the oligonucleotides in place in an array and then cleaving the oligonucleotides from the surface of the array after they have been synthesized. See, e.g., Geary et al. (Nature Methods 2004 1: 241-248) and LeProust et al. (Nucleic Acids Research 2010 38: 2522-2540).

As used herein, the term "multiple sets", in the context of a composition comprising multiple sets of oligonucleotides, refers to multiple distinct populations of oligonucleotides, where a set of oligonucleotides may comprise at least 2, at least 5, at least 10, at least 50, or at least 100 or more (e.g., 3 to 50, e.g., 4 to 30) of oligonucleotides and the composition may contain at least 5, at least 10, at least 50, at least 100, at least 500, at least 1,000 or at least 5,000 or more sets of oligonucleotides.

As used herein, the term "a set of double-stranded oligonucleotides that can be assembled to produce a synthon" and grammatical equivalents thereof refers to a set of oligonucleotides that can be enzymatically assembled into a longer sequence, referred to herein as a "synthon", that contains sequences from each of the oligonucleotides in a defined order. As would be understood, the double-stranded oligonucleotides of a set may contain: (i) an "indexing overhang" that hybridizes to an array and (ii) an assembly sequence, wherein the assembly sequences of each set of oligonucleotides can be assembled to produce a synthon, and (iii) a second "ligating overhang" on the opposite end of the duplex that is ligated to another similarly constructed double-stranded oligonucleotide.

The indexing overhang, is typically longer e.g. 20-40 nucleotides, whereas the ligating overhang is typically shorter, e.g. 1-10 nucleotides.

As used herein, the term "index-specific ordered ligation", refers to a protocol in which double-stranded fragments are ligated to one another to produce a synthon using DNA ligase, where the order of fragments in the synthon is dictated first by the distinctness of indexing overhangs, which define which oligonucleotides will become part of each synthon, and secondarily by a small number of distinct ligation overhangs sequence that are to be ligated within each array feature. Within a feature the order of ligation is determined by the ovarhang sequence, and the cleavage of index overhangs, making a new overhang available at each subsequent stage of ligation of a long synthon. Ligation ordered simply by overhangs is far more limited in specificity than the present method. By using index-specific ordered ligation and having the oligonucleotides available for each construct constrained by the index sequence of the probes on the surface on the array, not merely by their ligating overhang sequence. The ligating overhang is helpful when there is a multi-step ligation process (e.g. 4-part, 8-part, or 16-part assembly), as the different parts within a feature will not cross-ligate if their ligating overhangs are distinct. However the use of indexing overhangs also allows far shorter and less complex overhangs. Distinct synthons can share overhangs without appreciable cross-talk. This is an unexpected benefit and improvement over previous high-throughput methods.

As used herein, the term "indexer sequence" refers to a unique sequence that occurs at in one overhang of a double-stranded oligonucleotide, wherein the oligonucleotides within each set of oligonucleotides for each synthon have the same distinct indexer sequence and each set of oligonucleotides has a different indexer sequence than all other synthons. Indexer sequences are different from one another and from their complements. For example, a first unique sequence has a different nucleotide sequence than a second unique sequence or its complement. Indexer sequences do not hybridize to each other, i.e., they have been designed so that they do not anneal to one another under stringent conditions. Such sequences, called "sequence tokens" in certain publications, are described in, e.g., US20070259357 and Brenner et al (Proc. Natl. Acad. Sci 1992 89:5381-3), which are incorporated by reference herein. A terminal indexer sequence may be 8-50 bases in length, e.g., 10-35 bases in length, or 15-40 bases in length. In some instances, a terminal indexer sequence may be up to 100 bases in length.

As used herein, the term "spatially-separating" in the context of spatially-separating different sets of double-stranded oligonucleotides from one another, refers to separating different sets of oligonucleotides from one another such that the different sets of oligonucleotides are present at different locations on an array. Specifically, the oligonucleotides in a first set become associated with a first location on an array, the oligonucleotides in a second set become associated with a second location on the array, and the oligonucleotides in a third set become associated with a third location on the array, and so on. Association can be manifested by hybridization of a given set at a particular feature, such as at a feature having a probe of a particular sequence.

As used herein, the term "double stranded oligonucleotide" refers to an oligonucleotide molecule that is substantially double-stranded, e.g., contains a double stranded region of at least 50 base pairs, alternatively at least 30 base pairs.

The term "synthon", as used herein, refers to a synthetic nucleic acid that has been assembled in vitro from several shorter nucleic acids.

The term "surface-tethered", as used herein, refers to a molecule that is attached to a surface covalently or non-covalently.

The term "surface-distal end" refers to the end of a surface-tethered oligonucleotide that is furthest from the surface.

The term "surface-proximal end" refers to the end of a surface-tethered oligonucleotide that is closest to the surface.

The term "overhang" refers to a single-stranded region at the end of a double-stranded oligonucleotide. An overhang can be a 5' overhang (in which case the 3' end is recessed) or a 3' overhang (in which the 5' end is recessed).

The term "ligation compatible" refers to two overhangs of the same length that are complementary to one another. Such overhangs can be ligated together by a ligase.

Other definitions of terms may appear throughout the specification.

Description

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated front or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

This disclosure provides, among other things, a method for assembling a synthon by index-specific ordered ligation on a support. The method may be used to produce synthon by ligating sequences from two, three or four or more double-stranded oligonucleotides in a defined order. As will be described in greater detail below, the method may be multiplexed in that a plurality of different synthons (e.g., at least 2, at least 10, at least 100, at least 1,000 or at least 10,000, or at least 100,000 synthons) can be produced on the same substrate, where each synthon is produced in a feature of the substrate. The first steps of the method generally involve hybridizing a first double-stranded oligonucleotide and a second double-stranded oligonucleotide to a substrate comprising surfece-tethered oligonucleotides, and ligating the surface-distal ends of the first and second double-stranded oligonucleotides together, thereby producing a first ligation product that is tethered to the support at both ends. One end of this product can be cleaved from the support, thereby producing another overhang that can be ligated to other double-stranded molecules that are on the support within the same feature and contain ligation compatible overhangs. This process can be repeated several times in the production of a single set of synthons.

Figure 1:
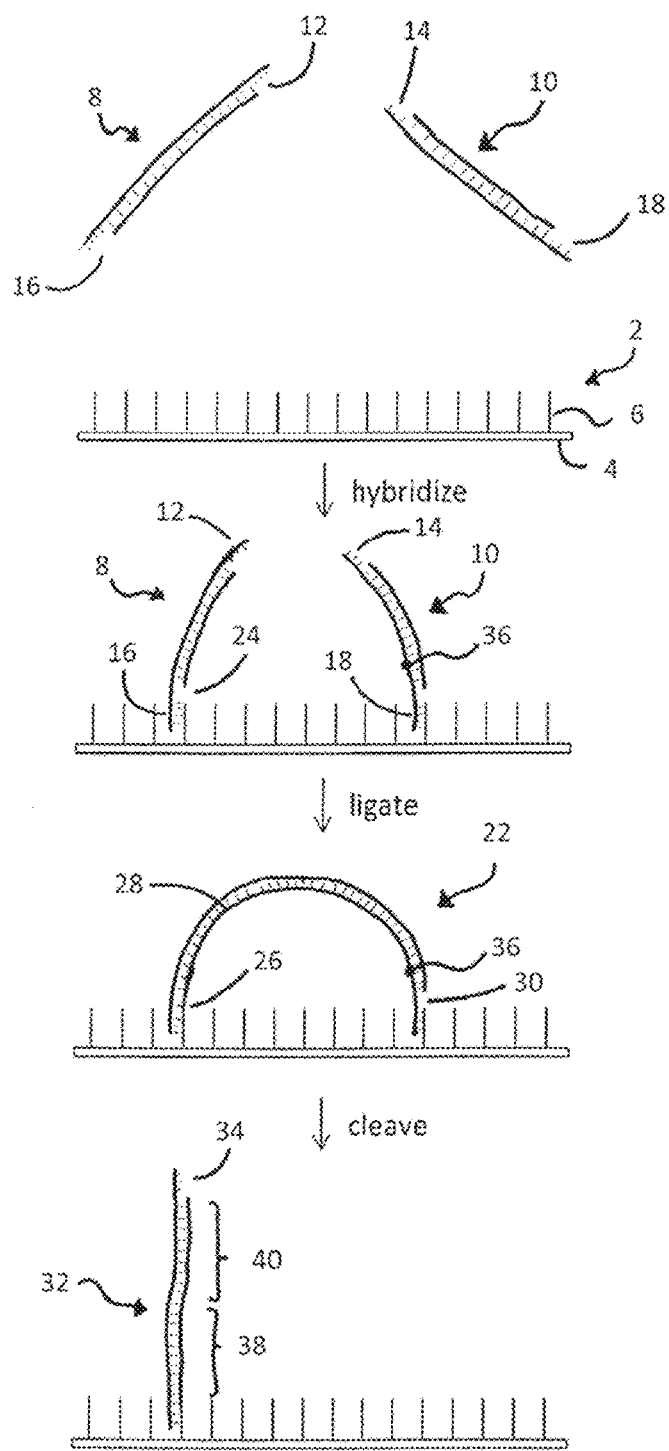
Figure 2:
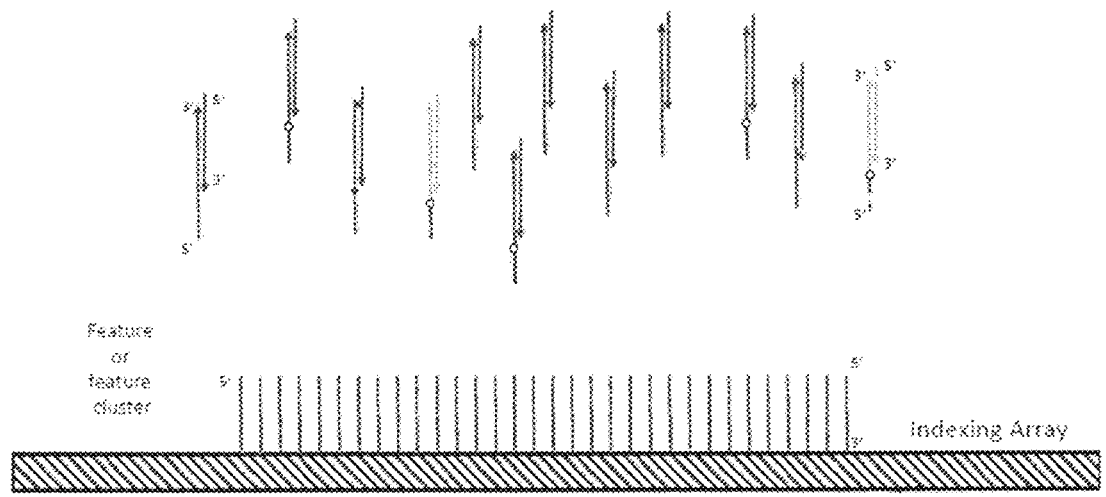

With reference to FIG. 1, some embodiments of the method may comprise obtaining: (i) a substrate 2 comprising a support 4 and a population of oligonucleotides 6 that are tethered to the support, (ii) a first double-stranded oligonucleotide 8 having overhangs at both ends (overhangs 12 and 16), and (iii) a second double-stranded oligonucleotide 10 having overhangs at both ends (overhangs 14 and 18). The oligonucleotides that are tethered to the support may be tethered by their 5' end or their 3' end, and they may be tethered covalently or non-co valently. In this method, the overhangs at the first end of the first and second double-stranded oligonucleotides (i.e., overhangs 12 and 14) are ligation compatible, whereas the overhangs at the second end of the first and second double-stranded oligonucleotides (i.e., overhangs 16 and 18) are each complementary to a surface-tethered oligonucleotide 6. The sequences of overhangs 16 and 18 can be the same or different, as long as they are complementary with and capable of hybridizing to a surface-tethered oligonucleotide 6. The sequences that hybridize to the surface-tethered oligonucleotides may be referred to as an "indexer" sequence in other parts of this disclosure.

The next step of the method involves hybridizing the first double-stranded oligonucleotide 8 and the second double-stranded oligonucleotide 10 with the surface-tethered oligonucleotides 6 to produce product 20. As shown in FIG. 1, this hybridization step results in hybridization of the second ends of the first and second oligonucleotides (i.e., the ends of double stranded oligonucleotides 8 and 10 that contain overhangs 16 and 18) to different surface-tethered oligonucleotides, thereby tethering the second ends of the first and second double-stranded oligonucleotides to the support. The substrate comprises both double-stranded oligonucleotides in their double-stranded form.

Next, the method involves ligating the first ends (i.e., compatible overhangs 12 and 14) of the first end of first and second double-stranded oligonucleotides (which are now distal to the surface of the support) together, thereby producing a first ligation product 22 that is tethered to the support at both ends. Since the overhangs of the oligonucleotides have compatible ends, the oligonucleotides do not need to be filled in, chewed back or otherwise made blunt, and the ligation does not need to be mediated by a split. As shown, both strands of the first double-stranded oligonucleotide are ligated to the second double stranded oligonucleotide to produce first ligation product 22.

As would be understood, the double-stranded oligonucleotides are synthetically made molecules, not fragments of genome, cDNA or in any way derived from living entity. The double-stranded oligonucleotides may be made by hybridizing two or more complementary single-stranded oligonucleotides to one other to make a duplex that comprises a double-stranded region with overhangs at both ends. In any embodiments, the double-stranded oligonucleotides may have a double-stranded region of at least 30 base pairs, at least 50 base pairs, at least 100 base pairs, at least 150 base pairs or at least 200 base pairs, depending on the length of the desired product and how the method is implemented. The lengths of the overhangs may vary and, in some embodiments, may be in the range of 1 to 40 bases in length. In some embodiments, the distal overhangs that are at the first end of the first and second double-stranded oligonucleotides (i.e., the overhangs that are ligated together) may be in the range of 1 to 9 bases in length and, as such, may have a 5' or 3' overhang of 1, 2, 3, 4, 5, 6, 7, 8, or 9 bases in length. The overhangs at the other proximal end of the second double-stranded oligonucleotides, i.e., the "second" end which is hybridized to the substrate, may be in the range of 10 to 40 nucleotides in length, e.g., 12-30 nucleotides in length. The indexing overhangs are at 5'-ends of the double-stranded oligonucleotide when the probes on the array are attached to the solid support at their 3' ends, such as constructed by conventional synthesis. In embodiments where the probes are attached to the solid support at their 5' ends, a 3' overhang is required for the proximal end of the double-stranded oligonucleotides. As noted below, the double-stranded oligonucleotides may be treated with mutS, a DNA mismatch binding protein from *Thermus aquaticus*, thereby removing any double-stranded oligonucleotides that do not have perfectly complementary sequences (i.e., contain a "bulge"). As may be apparent, any hybridizing step (e.g., the step during which the overhangs at the second end of the first and second double-stranded oligonucleotides are hybridized to the tethered oligonucleotides on the support) should done under conditions that do not denature the first and second double-stranded oligonucleotides. In some embodiments, the hybridizing is done at a temperature of 45° C. to 70° C., alternatively 55° C. to 70° C., or equivalent conditions thereof, depending on the length of the indexing sequences and the buffer conditions. The temperature and buffer conditions may be selected to minimize non-specific hybridization of oligonucleotides that are intended for a different feature, while not substantially reducing specific binding between oligonucleotides. Such conditions are relatively straightforward to determine given the large difference in $T_m$s of the double-stranded region and the overhangs.

In some embodiments, a double-stranded oligonucleotide may be composed of complementary single-stranded oligonucleotides that are hybridized together. In other embodiments, the double-stranded oligonucleotide is comprised of a long single-stranded oligonucleotide with a hairpin at one end, and that single-stranded oligonucleotide is cleaved within the hairpin to form an oligonucleotide having an overhang. The hairpin will generally be cleaved prior to ligation, for example, by cleaving with a type II restriction enzyme, leaving an overhang at the end to be ligated. This latter embodiment enables the synthesis and construction of synthons with long homologous or even identical sequences in some regions of the assembly while avoiding incorrect cross hybridization of oligonucleotides in solution before hybridization to the array. In some embodiments, the double-stranded regions of the double-stranded oligonucleotide contribute some portions of the synthon, and the remaining portions are filled in using a DNA-polymerase after a first ligation step, such that the filled-in portion is contributed by an overhang. This allows a constant sequence to be shared across multiple synthons while avoiding or reducing cross-hybridization across the variable single-stranded regions.

In some embodiments, the first double stranded oligonucleotide may be designed so that the recessed strand of the second end of that oligonucleotide is ligatable to the surface-tethered oligonucleotide after hybridization of the first double stranded oligonucleotide to the surface-tethered oligonucleotide. As shown in FIG. 1, in some embodiments, the complex produced by hybridization of the first double-stranded oligonucleotide to a surface tethered oligonucleotide may contain a nick 24 that can be sealed with a ligase. In these embodiments, the ligation step may also ligate the second end of the first double-stranded oligonucleotide to a surface-tethered oligonucleotide to produce ligation junction 26. In these embodiments, the first ligation product 22 may comprise a strand 28 that contains the sequence of a surface tethered oligonucleotide, one of the strands of the first double-stranded oligonucleotide, and one of the strands of the second double-stranded oligonucleotide, in covalent linkage. In these embodiments, the second end of the second double-stranded oligonucleotide does not need to be ligated to a surface-tethered oligonucleotide. As such, in first ligation product 22, there may be a "gap" 30 between the end of one of the strands of the ligation product 22 and the surface-tethered oligonucleotide, although ligation between the second end of the second double-stranded oligonucleotide and the surface tethered oligonucleotide can be prevented by other means. Such embodiments allow the production of long single-stranded oligonucleotides that may be harvested by high temperature, above 90° C., or low salt denaturation of strands.

In some embodiments, the method may further comprise cleaving the second end of the second oligonucleotide to release one end of the first ligation product from the support to produce product 32. In these embodiments, cleavage can result in production of a new overhang 34 at the surface end distal of the first ligation product (i.e., the end that is not tethered to the support). This overhang, as will be described in greater detail below, can ligated to another molecule that has a compatible overhang. As illustrated, the cleavage step may be implemented using a restriction endonuclease or by cleaving a cleavable linkage 36 (which may be photocleavable or chemically cleavable). If a cleavable linkage is used, then the cleavage reaction may result in an end comprising a 3' hydroxyl or 5' phosphate (depending on which end is tethered to the substrate), thereby allowing that end to participate in another ligation, if needed. In some embodiments, the cleavable linkage may be 1 to 9 nucleotides (e.g., 1, 2, 3, 4, 5, or 6 or more nucleotides) upstream or downstream from the end of the other strand, thereby allowing for the production of an overhang when the linkage is cleaved. If the cleavage step does not leave a phosphate at the 5' end of the cleavage site, the end can be phosphorylated enzymatically by means of a kinase enzyme. Cleavage of such a linker can also release the end of the first ligation product from the substrate. As shown, product 32 contains a sequence 38 that is from the first double stranded oligonucleotide and a second sequence 40 that is from the second double-stranded oligonucleotide.

If a cleavable linker is used, then the linker may be chemically cleavable (e.g., using gaseous ammonia or another cleavant) or photocleavable, for example. In some instances, cleavage of a cleavable linker may result in a 3'-hydroxyl, while in other instances cleavage of a cleavable inker may result in a 5' phosphate. A suitable phosphoramidite that can be cleaved to produce a terminal 5'-phosphate is shown below. This and other suitable linkers that leave behind a 5'-terminal phosphate can be obtained from commercial sources.

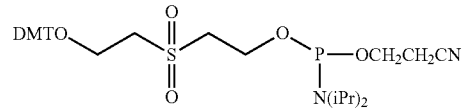

To generate a 3'-hydroxyl, suitable phosphoramidite monomers are known and include the Unylinker®-related phosphoramidite (US20040152905) and thymidine-succinyl hexamide CED phosphoramidite (Chemgenes). Use of the thymidine-succinyl hexamide CED phosphoramidite linker, will result in a 3' hydroxylated T residue at the 3'-end. Alternative linkers could be constructed so that the oligonucleotide is terminated by any desired base.

Photochemically cleavable linkers can also be used. A commercially available (Glen Research) photocleavable linker phosphoramidite that leaves behind the desired phosphate on the 5'-end is shown below.

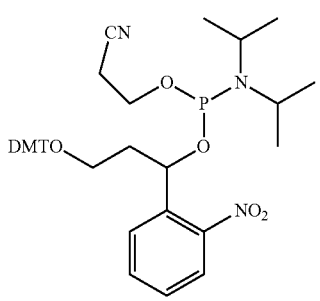

A suitable photocleavable linker that leaves behind a 3'-OH is shown below.

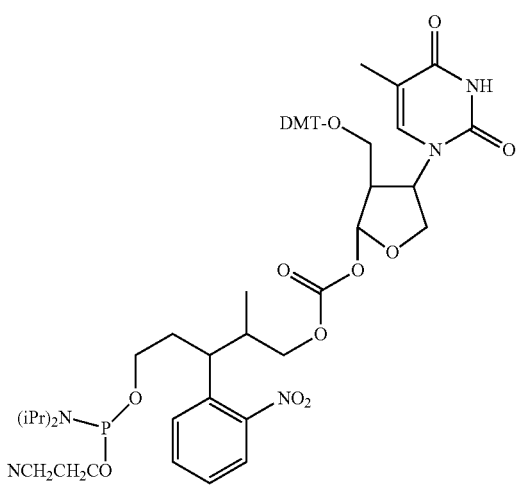

In embodiments in which new overhang 38 is produced, the method may further comprise ligating the overhang to a ligatably compatible overhang of another double-stranded nucleic acid. In some embodiments, the other double-stranded nucleic acid may be tethered to support 4. In these embodiments, the other double-stranded nucleic acid may be a third double-stranded oligonucleotide that is anchored to the support, or a ligation product containing the same, e.g., a ligation product containing the third double-stranded nucleic acid and a fourth double-stranded nucleic acid. As would be recognized, the end of the other double-stranded oligonucleotide or ligation product containing the same can be designed to have an overhang that is compatible with overhang 34, thereby allowing the production of another ligation product—a "second" ligation product—that is tethered to the solid support at both ends. In these embodiments the method may further comprise cleaving an end of the second ligation product (e.g., using a chemical, photocleavable linkage), thereby releasing one end of the second ligation product from the support. The released end of the second ligation product can be designed to contain another overhang, which again can be joined to another double-stranded oligonucleotide or ligation product containing the same, thereby allowing the second ligation product to be extended. As such, in some embodiments, the method may be used to make a synthon of any length.

In some embodiments, the overhang at the end of the first ligation product may be ligated to a third double-stranded oligonucleotide, wherein the third double-stranded oligonucleotide has a first end that is tethered to the support (e.g., hybridized to or covalently linked with) and a second end that has an overhang that is ligation compatible with the overhang at the end of the first ligation product.

In other embodiments, the overhang at the end of the first ligation product may by ligated to another construct, wherein the other construct product comprises the third double-stranded oligonucleotide, and wherein the other construct has a first end that is tethered to (e.g., hybridized to or covalently linked with) the support and a second end that has an overhang that is ligation compatible with the overhang at the end of the first ligation product. As described in greater detail below, the other construct may be made in the same way as the first ligation product, i.e., by hybridizing the support with two double-stranded oligonucleotides that have overhangs at both ends (i.e., a third and a fourth double stranded oligonucleotide), where the overhang at one end of both double-stranded oligonucleotides hybridizes to the tethered oligonucleotides on the support, and the other end of both double-stranded oligonucleotides are ligation compatible, ligating the compatible ends together to produce the other construct, and then cleaving one end of the construct to produce an overhang that is compatible with the overhang of the first ligation product.

After two ligation steps, a synthon can be produced from four double-stranded nucleotides. If the process is repeated a third time, a synthon can be produced from eight double-stranded nucleotides. Multiple repetitions of this process can be performed to produce longer synthons, taking into consideration the practical yields of successive ligation steps and the use of independent cleavable linkers or restriction enzymes. For example, different restriction enzymes could be used to cleave intermediate synthons at different sites and introduced at different steps in the process. Alternatively, two or more photocleavable linkers that are cleaved at different wavelengths can be utilized at different steps.

After a ligation product is made, the ligation product may be amplified. In some embodiments, the method may comprise amplifying the second ligation product, e.g., using PCR or another amplification method. If PCR is used, then the amplification may be done in a way that results in amplification products that are free in solution, or amplification products that are tethered to the support by at least one end. In some embodiments, the second ligation products may be cleaved from the support and then amplified.

In some embodiments, the support may be planar. In other embodiments, the support may be a bead or the like. In particular embodiments, the support may comprise multiple populations of surface-tethered oligonucleotides, wherein each population of surface-tethered oligonucleotides occupies a spatially distinct region on the support, e.g., in the form of an array. In additional embodiments, the support may be an array of microwells, nanowells or picowells. In these embodiments, multiple populations of double-stranded oligonucleotides may be produced, e.g., as a mixture, and the overhangs at the second ends of those oligonucleotides allow multiple sets of double-stranded oligonucleotides (i.e., where a "set" is composed of the oligonucleotides that are going to be ligated together) to be spatially separated from one another on the substrate, thereby allowing the double-stranded oligonucleotides of each set to be ligated together in a defined area without interference from double-stranded oligonucleotides from other sets. Thus, in some embodiments, each double-stranded oligonucleotide of a set will base the same or similar second overhang (i.e., the second overhang may comprise an "indexer" sequence) and the double-stranded oligonucleotides of different sets have different overhangs that hybridize to different regions of the indexing oligonucleotide that is bound to the substrate. In such embodiments, various double-stranded oligonucleotides can be ligated together in discrete spatially separated parts of a substrate. Because, after the initial hybridization step, all of the reactions involve molecules that are attached to the substrate, any treatments (e.g., washes, enzyme treatments, etc.) can be done by exposing all of the reactions to the treatment at the same time, e.g., by dipping the substrate into a solution containing the treatment, flooding the substrate with the treatment, or flowing the treatment across the top of the support, for example. In other embodiments, the reactions are kept separate from one another, and the various treatments are done in droplets on the surface of the support.

In such multiplex embodiments, the method may comprise obtaining a mixture of multiple sets of double-stranded oligonucleotides, where each set corresponds to a different synthon, and the double-stranded oligonucleotides for the different sets have different overhangs at their second end, thereby allowing them to be spatially separated on an array. Such double-stranded oligonucleotides can be made by synthesizing various single-stranded oligos in situ on the surface of the same substrate (e.g., using the methods of e.g., Clear et al., Nature Methods 2004 1: 241-248, LeProusi et al, Nucleic Acids Research 2010 38: 2522-2540), cleaving those oligonucleotides from the support and then hybridizing them together in solution. Each set of oligonucleotides can be assembled to produce a synthon, i.e., can be enzymatically assembled into a longer sequence that contains sequences from each of the double-stranded oligonucleotides in a defined order.

As noted above, the oligonucleotides within each set each may comprise the same "indexing" overhang and which allows them to be grouped on an array. In other words, the oligonucleotide within each set contain the same overhang, and the oligonucleotides in the different sets differ from one another by their overhang. In these embodiments, the method may comprise hybridizing the mixture of double-stranded oligonucleotide to an array, thereby spatially-separating the different sets of oligonucleotides from one another. In these embodiments, the double-stranded oligonucleotides of one set locate to one feature and the double-stranded oligonucleotides of another set locate to another feature.

In other embodiments two or more sets of double-stranded oligonucleotides bind to two or more sequences within the same feature. For example, this can be done by utilizing different regions of the feature for each double-stranded oligonucleotide or set, or by using a mixture of two or more probes attached to the solid support.

The synthons can then be collected in the aqueous phase and, in certain cases, amplified using primers (e.g., universal primers) that bind to sites at the ends of the synthons. Alternatively, a single strand of each synthon can be denatured from a second strand covalently linked to solid support by use of a high temperature stringent elution protocol. The method may be used to make at least 10, at least 50, at least 100, at least 500, at least 1,000, at least 5,000, at least 10,000, at least 50,000, or at least 100,000 synthons in parallel. In other embodiments, the synthons may by amplified in situ, i.e., while they are attached to the surface of the array, using primers that are in the solution phase.

The synthon itself can be of any sequence and, in certain cases, may encode a sequence of amino acids, i.e., may be a coding sequence. In other embodiments, the synthon can be a regulatory sequence such as a promoter or enhancer. In particular cases, the synthon may encode a regulatory RNA. In certain cases, a synthon may have a biological or structural function.

In particular cases, a synthon may be cloned into an expression vector designed for expression of the synthon. In these embodiments, the expression vector may contain a promoter, terminator and other necessary regulatory elements to effect transcription and in certain cases translation of the synthon, either as a single protein, or as a fusion with another protein. In these embodiments, the method may further comprises transferring the expression vector into a cell to produce the expression product (e.g., a protein) encoded by the synthon. This embodiment of the method may comprise screening the expression product for an activity.

An example of an implementation of this method, is set forth be low. In some embodiments, the method may involve;

1. Hybridizing pairs of complementary oligonucleotides in solution phase to produce double-stranded oligonucleotides;

2. Optionally treating the double-stranded oligonucleotides, e.g., using Mut-S, to reduce the number of double-stranded oligonucleotides that contain errors;

3. Hybridizing a mixture of double-stranded oligonucleotides to an array, thereby spatially separating different sets from double-stranded oligonucleotides from one another, where a "set" is composed of the double-stranded oligonucleotides that are going to be assembled together;

4. Washing away unbound oligonucleotides;

5. Adding ligase and to ligate pairs of double-stranded oligonucleotides together, and ligate some of the double-stranded oligonucleotides to an end of an oligonucleotide on the substrate;

6. Cleaving the overhanging ends (chemically, photochemically or by restriction enzyme);

7. Optionally treating the ligation products, e.g., with T7 endonuclease, to reduce the number of ligation products that contain errors;

8. Ligate the ligation products together to form a second bridge, and optionally a third bridge, a fourth bridge, or a higher order bridge.

9. Optionally repeating any of the steps 2 through 8 as many times as necessary to form synthons of the desired length, and increasing the synthon lengths by a factor of two with each successive ligation step.

A more in-depth description of each of these steps is set forth below. The following description provides an example of how the method can be implemented and is not intended to be limiting.

Prehybridize Pairs of Complementary Oligonucleotides in Solution Phase

Sets of DNA oligonucleotides are synthesized by a large scale process (e.g., using the methods of e.g., Cleary et al., Nature Methods 2004 1: 241-248, LeProust et al., Nucleic Acids Research 2010 38; 2522-2540), and designed so that they will hybridize to form long-double stranded DNA strands with single-stranded overhangs on both ends. On one end is a 5' overhang that is moderate length indexing sequences (10-40 nt) for the purpose of specifically attaching the duplex to a surface-tethered oligonucleotide within a feature on an array. Some, or even all, of these overhanging sequences are connected to the double stranded region by a cleavable linker sequence. On the opposite end is an overhang for the purposed of specific ordered assembly to form longer doubled stranded DNA. This overhang can be the either 3'-end or the 5'-end. These oligonucleotide pairs are depicted in solution in FIG. 1. The total length of the oligonucleotides may be between 100 and 400 nucleotides. In some embodiments, the overhang is substantially longer on the immobilizing portion of the oligonucleotide that hybridizes to the surface-bound probe. The 3'-end of the shorter oligonucleotide subsequently can be extended by DNA polymerase after a ligation step. This embodiment is advantageous in cases where two or more distinct oligonucleotides in the complex DNA mixture are so similar that they may non-specifically cross-hybridize, but contain an identical sequence in a region toward the ligating ends of the oligonucleotides. In such cases the polymerase may extend the shorter oligonucleotide to the end of each longer oligonucleotide. Alternatively, a DNA-polymerase without strand displacement activity can be employed to fill in only the single stranded region of the synthon, allowing it to be ligated again after a cleavage step.

In some embodiments, a double-stranded oligonucleotide is constructed from a long single-stranded oligonucleotide with a stable hairpin. In this embodiment, the hairpin can be cleaved using a Type II or IIS restriction enzyme leaving an overhang that can be ligated. Although this construction may appear a less efficient for making long oligonucleotides, it makes practical the construction of oligonucleotides that are difficult to anneal as perfect-matching double-stranded duplexes in complex mixtures, either due to homology between different distinct oligonucleotides, or due to secondary structures that may inhibit the annealing of complementary double-strand oligonucleotides. Type IIS restriction enzymes recognize asymmetric DNA sequences and cleave outside of their recognition sequence. Thus, type IIS restriction enzymes, in particular, offer an advantage over type II as their recognition sites can be incorporated into the stem of the hairpin to be cleaved and discarded, hence not part of the synthon. This has the advantage that the synthon can be any sequence, not constrained by containing a recognition sequence. In this embodiment, multiple restriction enzymes can be used at different stages involving multiple sequential bridge production.

In other embodiments utilizing DNA arrays attached to the surface at their 5'-ends, and free at their 3'-ends, the immobilizing overhang must be at the 3'-end of each of the double-stranded nucleotides.

In other embodiments, one strand or both strands of the double-stranded oligonucleotides to be ligated is comprised of RNA, and these oligonucleotides are ligated by RNA-ligase, such as T4 RNA ligase 2. This embodiment without RNA/DNA hybrids permits the construction of long single-stranded DNA oligos, by digestion of one strand by RNA digesting enzymes without the need for high temperature denaturation.

Error Reduce the Double Stranded Oligo Nucleotides in Solution by Mut-S

In some embodiments, it may be useful to perform error reduction by removal of bulge sequences by means of Mut-S, or another similar enzyme. Mut-S has the property that it binds to mismatched mis-matched bases and small single-stranded loops within double stranded DNA. See: Siying Ma, Ishtiaq Saaem, and Jingdong Tian, "Error Correction in Gene Synthesis Technology", *Trends Biotechnol.* 2012 March; 30(3): 147-154.

It can be used to remove sequences with synthesis errors if it is attached to beads (or other solid support) or if they are bound by antibodies that are themselves attached to beads (e.g. magnetic beads) and those beads are removed from the solution phase.

Hybridize a Mixture of Double-Stranded Oligonucleotides to an Indexing Array

Figure 3:
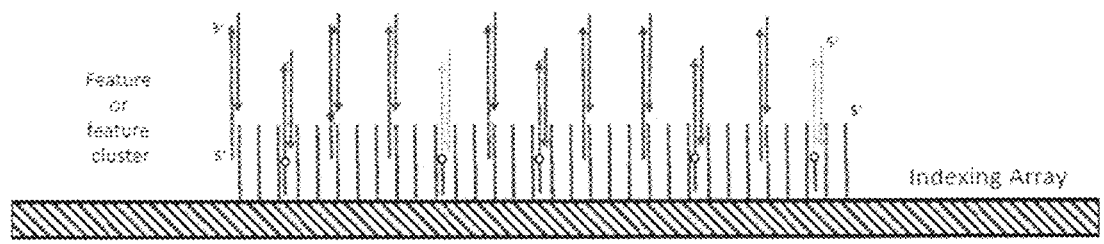

After error reduction, the mixture of double-stranded oligonucleotides is hybridized to an array. In some cases, the probe oligonucleotides (i.e., the oligonucleotides that are tethered to the array) are attached to the substrate at their 3'-ends. The product of this hybridization step is shown in FIG. 3. These probe oligonucleotides can be between 10 nucleotides and 100 nucleotides in length, and in some embodiments may be between 20 and 60 nt in length. In some embodiments, all duplexes targeted by a given index feature to include a common 5'-overhanging index sequence. In other embodiments, it can be advantageous for them to have two distinct indexing sequences for each target feature, where one subset is complementary toward the 3'-end of the index, probe, and another subset is complementary toward the 5'-end. This latter embodiment is depicted in FIG. 3.

This method may be performed in a flow cell, or an array of flow cells on a single slide, or between two slides. If two slides are used, then one or both slides may be used for the assembly. Reagents are flowed into the flow cell and flushed out after each step. The flow cell is also equipped with temperature control. The distance between the two slides or the top and bottom surfaces is minimized to minimize reagent volume while maximizing concentrations. Optimal conditions for hybridization to arrays are well known to those skilled in the art.

For example, a flow cell may be comprised of two slides pressed together into a sandwich contained within a metal housing. One of the slides may be a DNA array slide and the other slide may be a gasket slide for a "football field", 2-pack, 4-pack, or 8-pack format, as used for the commercial CGH applications (both available from Agilent Technologies). The gasket used on these slides provides a sufficient gap between the slides (about 400 um) to insert 30-gange needles (about 310 microns). Needles may be used to inject reagents between to the flow cell formed by the slides and to elute product. Typically, two needles are inserted through the gasket at opposite corners of each well. One is used to inject or elute reagents and another, at the opposite corner, is used to allow air move in and out of the cell and maintain the pressure at ambient. A metal housing can spatially constrain the slides and has one surface that is in direct contact with one slide, typically the DNA slide. The slides may be held vertical with one needle with reagent at the bottom and the other for air at the top. A metal surface may be temperature controlled, for example, using Peltier coolers for any temperature between 4° C. and 100° C. Typically, ligation may be performed at 16° C., and denaturation of product anywhere between 50° C. and 80° C. This arrangement can also be used for hybridization of oligonucleotides to an array. The flow of reagents into and out of the cell can be automated robotically.

Wash Away Unbound Oligonucleotides

After hybridization, the incomplete structures and unbound oligonucleotides are washed away with a stringent wash solution and at a stringent temperature. This stringency ensures that each chemical feature only has oligonucleotides for the construct to be assembled on that feature. This step removes many incompletely synthesized oligonucleotides, since they are usually synthesized from their 3'-ends to their 5'-ends.

Add Ligme and Assemble Double Stranded Oligonucleotides (Ligate Some to 5'-End of Probe Oligo)

Figure 4:
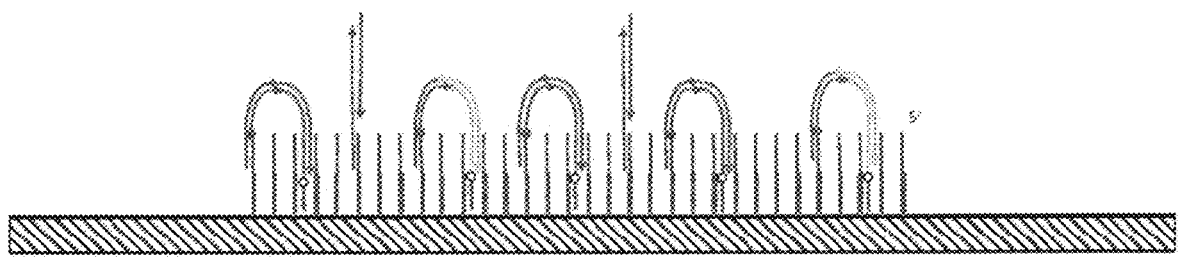

A mixture of ligase and ligase buffer (with the appropriate cofactor, ATP or NAD) is added to the flow cell to ligate the shorter overhanging ends of the double-stranded oligonucleotides to each other, as shown in FIG. 4. Only those overhangs that are complementary are ligated by the enzymes. Further, that complementarity is used to define the order of assembly of the parts to make the full-length synthons. The ligase enzymes that are most useful for this process are those that have good activity at a temperature where the probe oligonucleotides remain annealed, and have stronger activity for overhanging ends than for blunt ends. This is compatible with most non-thermostable enzymes. Good examples of these enzymes include T7-ligase and T4-ligase (NEB, Enzymaties or Qiagen). See, e.g., Pohl et al (Eur. J. Biochem. 1982 123: 141-52) and Ferretti et al (Nucleic Acids Research 1981 9: 85).

Optionally, it is useful for some downstream process for some of the constructs to be ligated to the capture probes. This can be easily done by designing the oligonucleotides so that their recessed end is immediately adjacent to the end of a surface-tethered oligonucleotide on the array. The oligonucleotides that will be ligated in this way are those at the 3'-end of the final fill length construct. For this to be possible, the surface-tethered oligonucleotides may have a phosphate group at their exposed 5'-ends. FIG. 4 depicts the assembled oligonucleotides forming bridges between tethered probes on the array, with oligonucleotides ligated to the capture probe indicated by a dot.

Cleave Overhanging Ends (Chemically, Photo-Chemically or by Restriction Enzyme)

Figure 5:
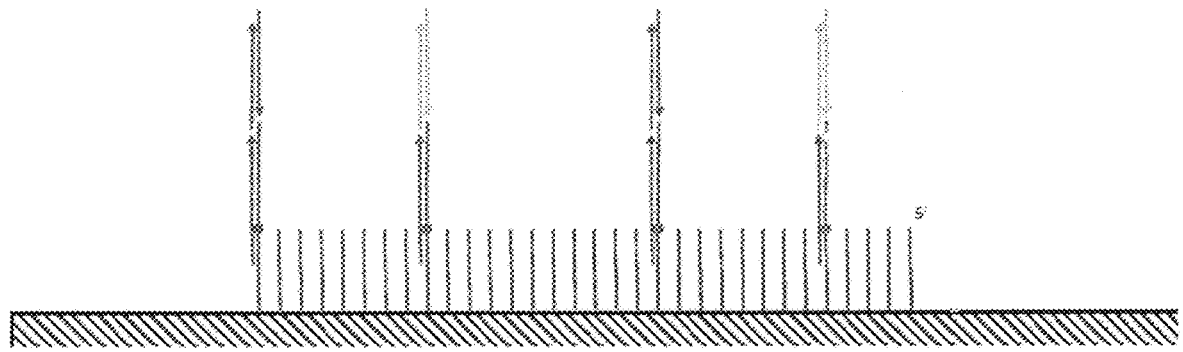
FIG. 5 illustrates a cleaved ligation product that has a defined overhang that is distal to the support. The cleavage can be done chemically, photochemically, or using a restriction enzyme).

One end of each bridge construct can be liberated by cleaving the overhanging one end of each ligated duplex, and, if necessary, melting a way the overhanging fragments by increasing the temperature (but not so high as to melt the duplexes of the longer constructs). This cleavage can be accomplished enzymatically by a restriction enzyme, or chemically by cleavable linkers. The cleavable linkers (represented by small circles in FIG. 4) can be photocleavable or chemically cleavable, depending on the efficiencies of available chemistries. Cleavage of the overhang does not leave a blunt end, but leaves a short overhang of a few (1-10) nucleotides to allow for specific ligation of the constructs, shown in FIG. 5. After cleavage of the overhangs, the 5'-ends of the remaining construct may need to be repaired by addition of a phosphate (using a kinase), depending on the cleavable linker chemistry used.

Error Reduction by T7 Endonuclease (Optional)

A second complementary error reduction approach that uses T7-endonuclease I can be employed here. This enzyme recognizes unmatched DNA, including cruciforms, Holliday structures, junctions and heteroduplexes, then cleaves the duplex oligonucleotides with errors at a phosphate linkage 5' to the mismatched regions. At this point, the flow cell can be heated to denature the double-strands, if error reduction is performed, the array is stringently washed while hot to remove cleaved fragments.

Figure 6:
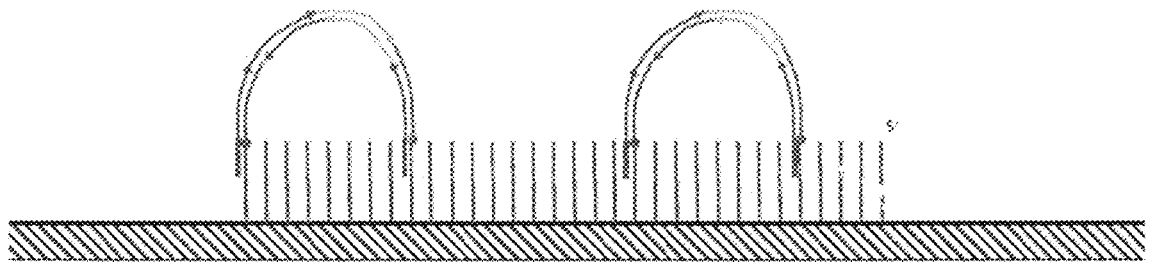
FIG. 6 illustrates how two different ligation products can be joined together by ligation, to produce a bridge.
Figure 7:
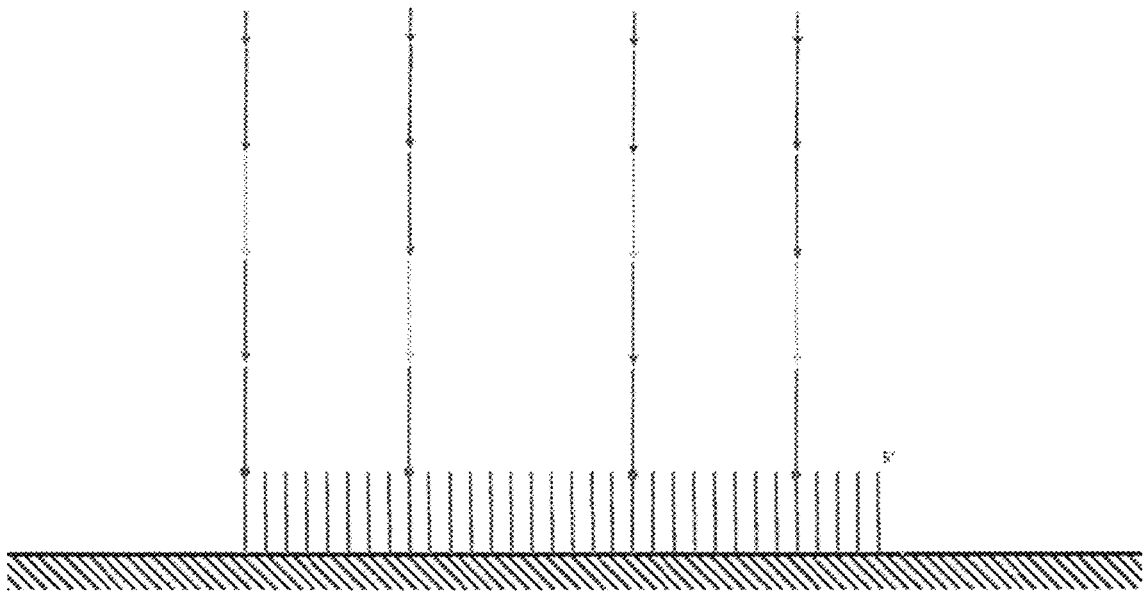
FIG. 7 illustrates an alternative assembly method that uses single stranded oligonucleotides. Oligonucleotides are liberated from the surface at one end and denatured by increasing temperature.

Ligation of Two-Oligo Products to Form a Second Bridge, a Third Bridge, or a Fourth Bridge As above, a mixture of ligase and ligase buffer is added to the flow cell to ligate the shorter overhanging ends of the double-stranded constructs to each other, as shown in FIG. 6. Again, only those overhangs that are complementary are ligated by the enzymes. Full length constructs now include four of the original synthesize oligonucleotides, nearly quadrupling the overall length of the original synthesis. As shown in FIG. 7, both strands of a completed synthon may be bond to the support. Ligation of oligonucleotide products may be continued to form a third bridge, a fourth bridge, and higher order bridges.

At this point the synthons can be optionally harvested by cleaving them from the array, e.g., using restriction enzyme or orthogonal cleavable linker, and amplified en masse. Alternatively, the synthons can be amplified without cleaving them from the array, e.g., using conventional PCR. In these embodiments, the PGR can be performed in bulk by filling the whole flow cell chamber with master mix and thermally cycling. Alternatively, the amplification reaction can be performed in droplets on the surface of the support, as described in US20150361422.

EXAMPLES

Aspects of the present teachings can be further understood in light of the following examples, which should not be construed as limiting the scope of the present teachings in any way.

Several steps of the protocol described above have been demonstrated experimentally. Particularly, the first ligation step in which two double stranded oligonucleotides are ligated together on an array has been demonstrated, with ligation yields up to 80%.

Example 1

In this experiment, two 80 nt oligonucleotides and two 50 nt oligonucleotides were kinased (to phosphorylate their 5' ends) and hybridized to each other in solution. 100 pmoles of oligonucleotides were hybridized in 1 ml hyb buffer to a microarray at 55° C. for 13 hours.

Figure 8:
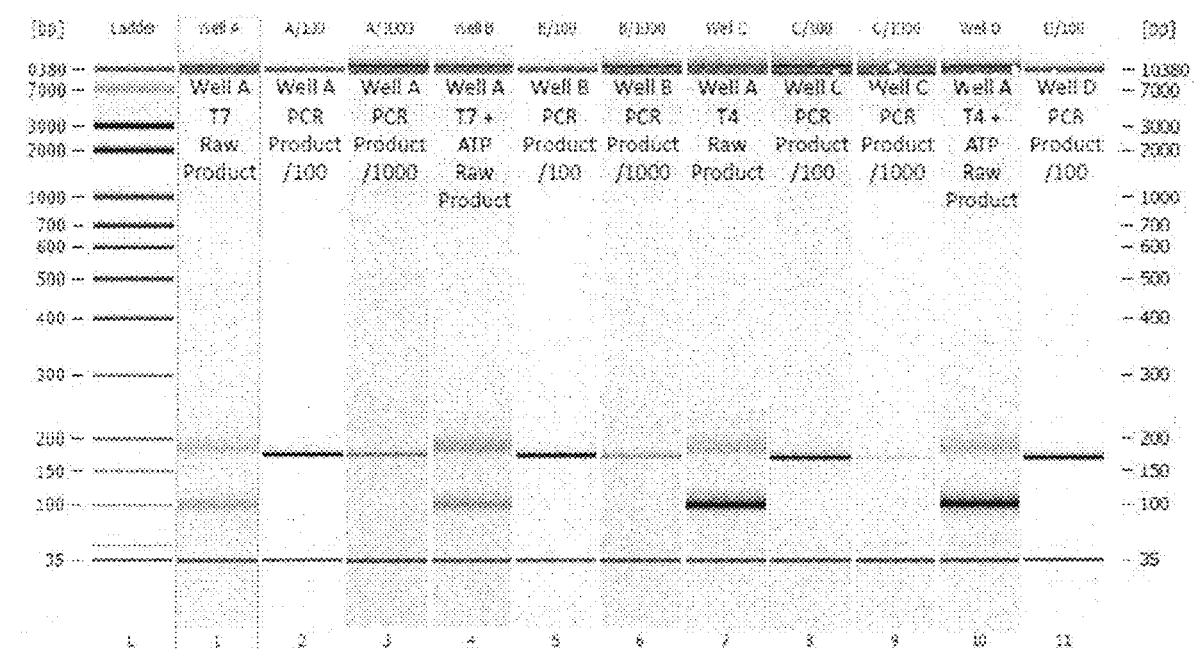
FIG. 8 shows the raw results of a ligation products (in 150 uL), produced by a BioAnalyzer.
Figure 9:
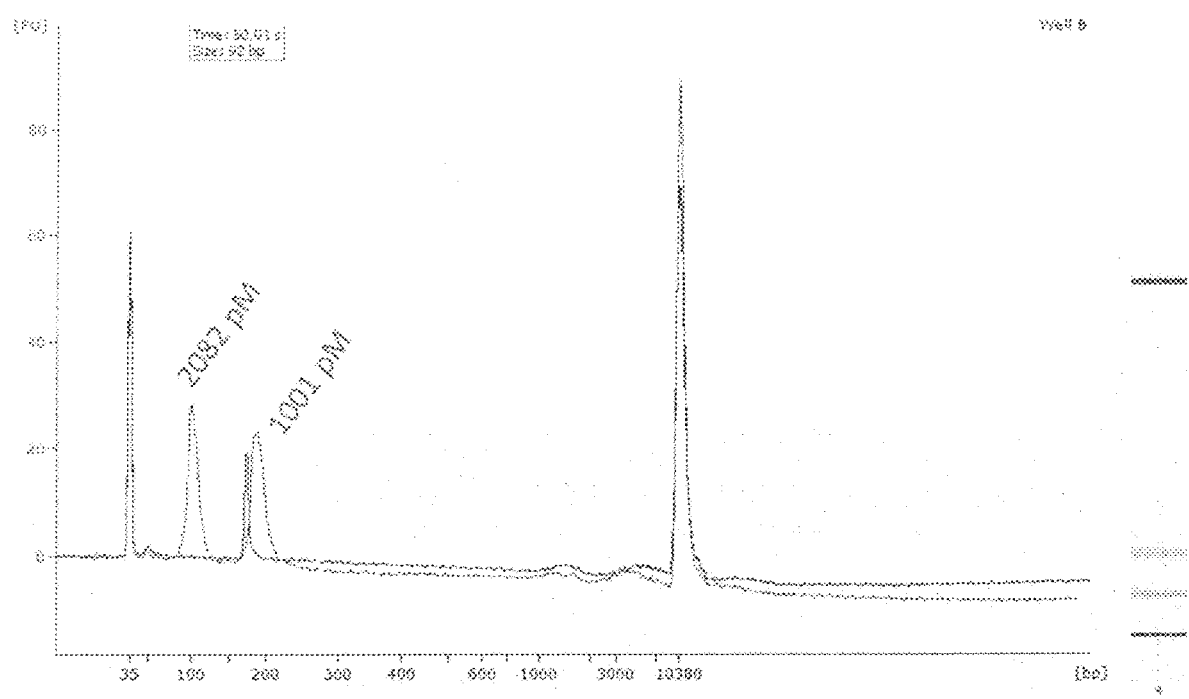
FIG. 9 is a graph showing an analysis of the products of well B.
Figure 10:
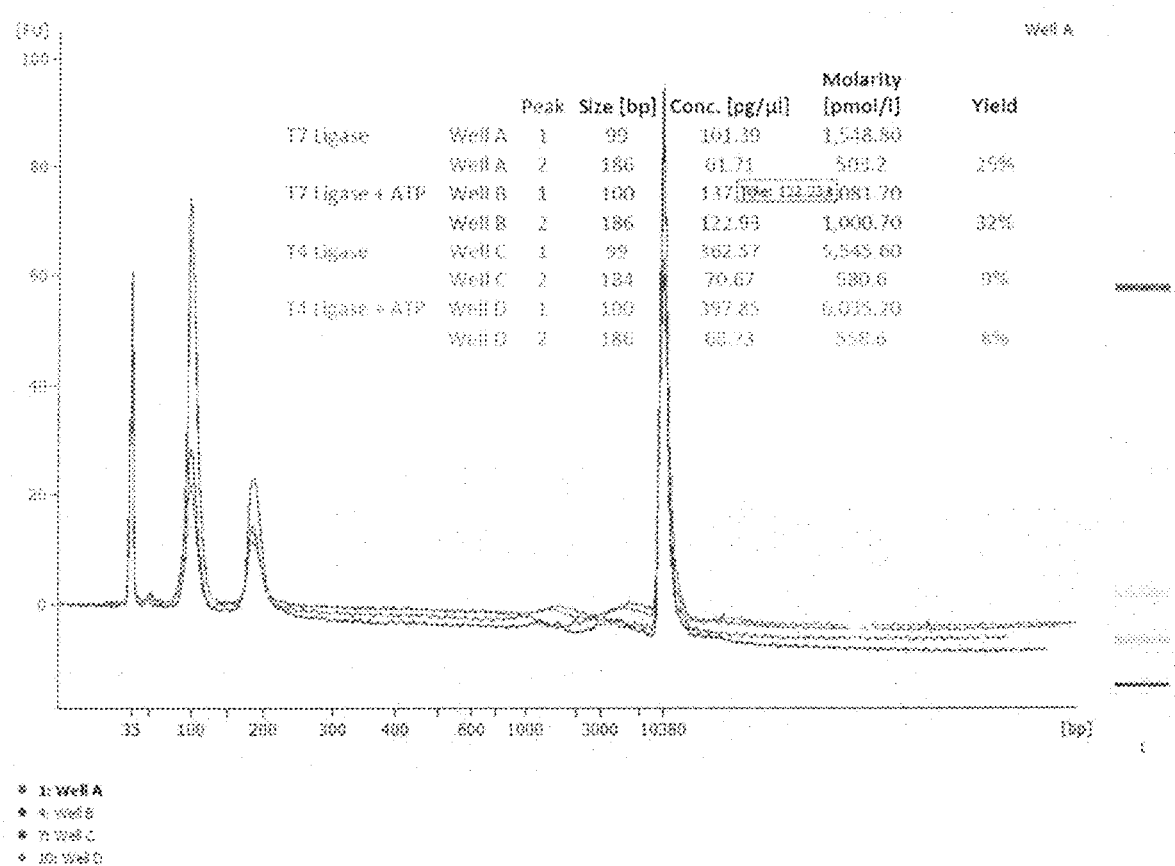
FIG. 10 is a graph showing an analysis of the products of wells A-D.

A four-well chamber was cooled to 3° C. on a temperature controlled block and kept cool during loading. A first array was loaded with an enzyme mix with 84,000 units T7 ligase and nominal ATP with needle and syringe. The well was quickly eluted leaving droplets of enzyme on the surface. And the chamber was backfilled with fluorinated oil (Novek 7500) to preserve the droplets. 30 ul of 10 mM solution of ATP was added to the elution from the first well and injected into a second. The same procedure was followed for a third and fourth well using T4 ligase. The apparatus was warmed to 20 degrees for 30 minutes, then warmed to 25° C. for an additional 30 minutes. The oil was removed from each well. 150 ul of water was added to each well and the apparatus was heated to 60 degrees C. The products were removed with a needle and syringe. The samples were analyzed using a High-Sensitivity Bioanalyzer chip along with a PCR product of the product of the first well. These results are shown in FIGS. 8-10. These traces show peaks with a shorter band consisting of the original double-stranded oligonucleotides at about 100 bp, and longer bands at about 200 bp consistent with the ligated products. The results indicate reaction yields from about 8% to 32%. These conditions have not been optimized and it is expected that much greater efficiencies can be achieved after optimization.

Example 2

In this experiment, efficient ligation of 2-part assemblies was demonstrated utilizing two 80 nt oligonucleotides and two 50 nt oligonucleotides that were obtained from and PAGE-purified by IDT. Synthesized oligos from 3rd party vendors do not have phosphate groups at their 5'-ends, unless that modification is specified. In those cases where the oligos that were to be ligated at their 5'-ends are not phosphorylated during synthesis, the oligos must be kinased to add a 5' phosphate group. In these experiments that phosphorylation was done using T4 polynucleotide kinase (PNK) from NEB (M0201S) and the protocol specified by the manufacturer sometimes in the specified kinase buffer and other times in T4-ligase buffer.

Oligonucleotides are pre-annealed in the following manner. Pairs of complementary oligonucleotides were mixed with an excess of the shorter oligonucleotides without the indexing sequence relative to its longer partner with an indexing sequence. Concentrations were in the range of 10 to 100 µM using any buffer amenable to annealing, including T4 ligase buffer. The oligonucleotides were heated to 80° C., then slowly cooled to 4° C. When phosphorylation of oligonucleotides was necessary, these two steps were combined in the same reaction and ran on the thermal cycler.

For a hybridization reaction, all 4 oligos (two pairs of duplexes) were mixed and diluted to a concentration of 8 µM (duplex concentration). The longer oligonucleotide of each duplex was hybridized via a 30 nt single strand to a complementary sequence on the 5' end of a 60 bp probe, and the other duplex was bound via a distinct 30 bp sequence complementary to the 3' end of the same probe on the array. The excess of the shorter oligonucleotide relative to its longer partner was to ensure that the vast majority of longer oligonucleotides annealed to the array would have complementary partners. Each reaction was performed with only single set of oligonucleotides to enable read-out using a BioAnalyzer™, so as to measure ligation efficiencies. The oligo mixture (25 µL) was mixed with 400 µL Agilent's CGB Hybridization Buffer (P/N 5188-5221) and 400 µL of water. 520 µL of that mixture was hybridized to a full-slide 244k format array using Agilent's SureHyb chamber at a temperature of 50° C., with a rotation period of 10 s. For convenience, typical hybridizations were run overnight, but, given the simplicity of the mixture and the excess of solution phase oligonucleotides, much shorter hybridization times are likely just as effective.

A relatively low stringent wash was used. The slide was dipped into a bath of Agilent CGH Wash-1 solution for 1 minute, then blown dry with nitrogen.

Ligation reactions can be performed in any array format. In this experiment, a 4-pack format was used to allow four simultaneous reactions, each in a different well. A ligation solution was prepared with NEB's T4-DNA ligase (M0202L) in ligase buffer. Ligase concentrations varied from 0.5 µL to 4 µL, each into a solution of 150 µL, with little impact on assay performance. A sandwich comprising an Agilent gasket slide (G534-60013) and an array slide was assembled, and each well was filled with approximately 100 µL of ligase solution. The assembly was held at 16° C., the recommended temperature for the T4 ligase enzyme. For convenience, the ligation reaction was ran for more than 8 hours, although the reaction goes to completion in far less time, on the order of a few minutes. (Subsequent reactions in similar experiments were run for 10 minutes with similar results.)

After the ligation, the solution was eluted from the wells and each well was refilled with nuclease-free water. For harvesting the temperature was raised to 50° C., the product of wells A & B were eluted, then refilled and elated at 60° C., and again at 70° C., and wells C & D were eluted at just 70° C. For the purpose of concentrating the products, the solution from each well was lyophilized, then rehydrated with 5 µL water, of which 1 uL was analyzed.

Figure 11:
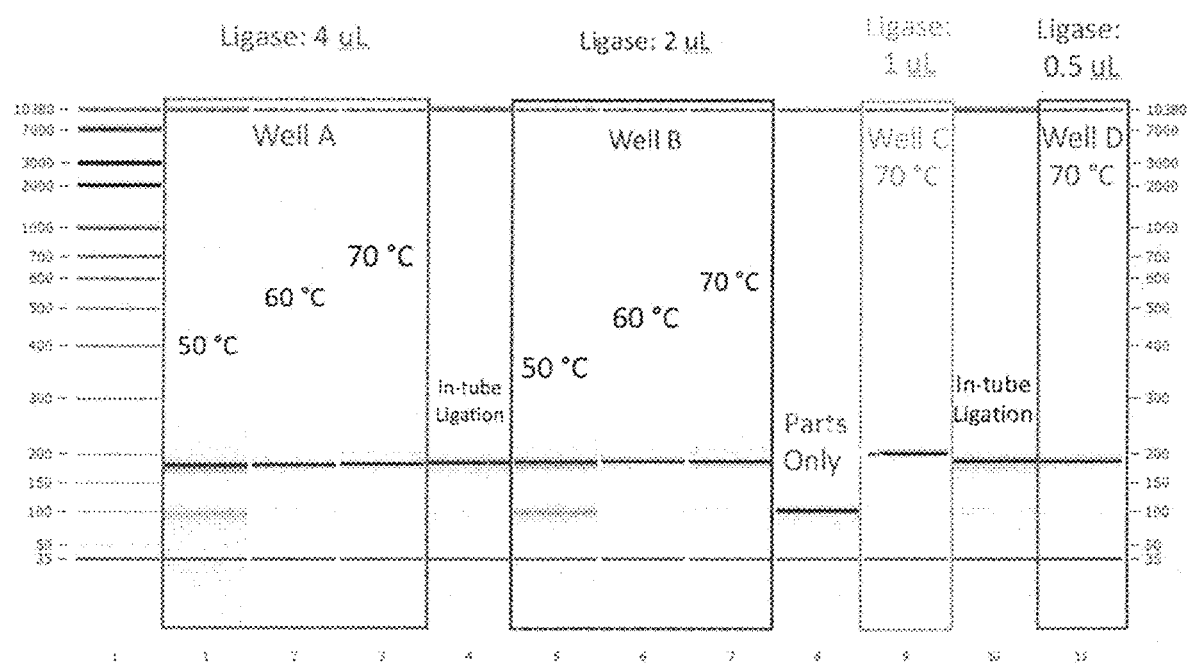
FIG. 11 is gel-formatted plot for 4 wells of samples analyzed on an Agilent BioAnalyzer.
Figure 12:
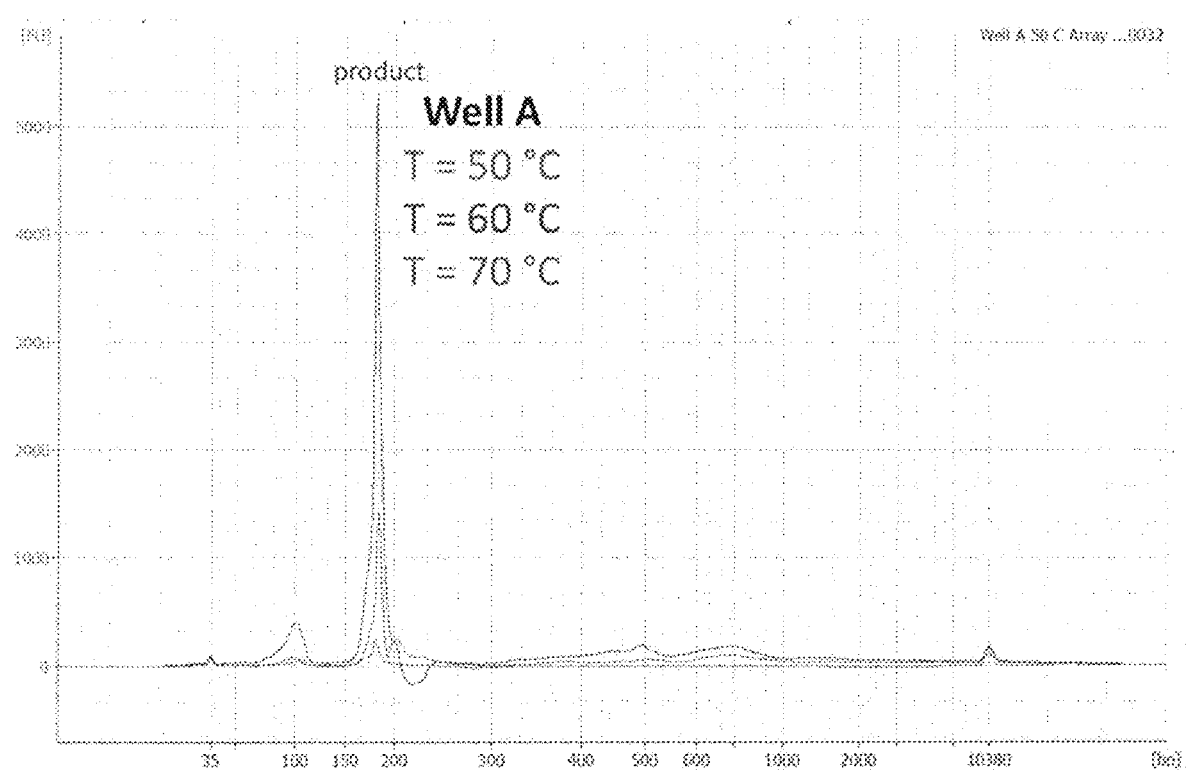
FIG. 12 shows electropherograms for Well A of FIG. 11.

The samples were analyzed on an Agilent BioAnalyzer, using Agilent's High-Sensitivity DNA kit (5067-4626). The Gel-formatted plot for all 4 wells is shown in FIG. 11. Dark bands can clearly be seen at about 180 bp in all lanes except lane which had the duplex oligo subassemblies ("parts only"). Lane 4 indicates the positive control construct ligated in a microtube. Lanes 1-3, indicate the contents of Well A for products eiuted at 50° C., 60° C. and 70° C. from on DNA-array. Similarly, lane 5-6 for Well B. The arrays contained in Wells C & D were only eiuted at 70° C. The four different wells had different amounts of T4-ligase enzyme with the 4 µL in Well A, decreasing by factors of 2 to the least in Well D, with 0.5 µL, FIG. 12 shows electropherograms for Well A for on-array ligation products eiuted at 50° C., 60° C., and 70° C.

Reaction yields were estimated by calculating the ratio of the concentration of the full length product to the sum of the concentrations of constituents plus product, as given in the table shown in FIG. 13. The yields for the total of each reaction were in the range of 74% to 83%. There did not seem to be significant reductions in yield with lower concentrations of enzyme, indicating that further reduction may be practical. Also, it was found that due to entropic effects related to the hybridization of ligation products at both ends, better purity of full-length product could be attained by use of serial elutions at several increasing temperatures, as unligated input material has slightly lower melting temperature.

The following sequences used in this demonstration of 2-part assembly (5' to 3'):

Part B1-Forward Strand:
(SEQ ID NO: 1)
CATGCTACGTATCGCAGTGATTGCACAACGAGATGACTCAGGCGGACCTC
TTATCTGCGATGGCATCTTGCAGGGCACGA Part B1-Reverse Strand:
(SEQ ID NO: 2)
ATTAGTATAAATGGCAGGTACCCCTGGCTTGCCGCAGGGACTGGCCCAT Part B2-Forward Strand:
(SEQ ID NO: 3)
GGGGTGATGGAGCCCCAACCGGAAGCAAGACACTTTGAACCGGGTTTCGG Part B2- Reverse Strand:
(SEQ ID NO: 4)
CTATACGACTCTAGGCGTGTACCATGTGGTCCAGCGTTCTTCATCATCGT
ATCTTTGATCCAAGAATTAAATTTGATCAA Part A1-Forward Strand:
(SEQ ID NO: 5)
CATGCTACGTATCGCAGTGATTGCACAACGGACGTAATGCTTTGTGCTGG
CGAAATGGGAGGGGAAAAGATACGTGTAG Part A1-Reverse Strand:
(SEQ ID NO: 6)
TCATCTCTACACGTATCTTTTCCCCCTCCCATTTCGCCAGCACAAAGCAT Part A2-Forward Strand:
(SEQ ID NO: 7)
AGATGACTCAGGCGGACCTCTTATCTGCGATGGCATCTTGCAGGGCACGA Part A2-Reverse strand:
(SEQ ID NO: 8)
CATGCTACGTATCGCAGTGATTGCACAACGGACGTAATGCTTTGTGCTGG
CGAAATGGGAGGGGAAAAGATACGTGTAG Index1_on_Index2
(SEQ ID NO: 9)
CGTTGTGCAATCACTGCGATACGTAGCATGACCACATGGTACACGCCTAG
AGTCGTATAG -continued Index2_on_Index1
(SEQ ID NO: 10)
ACCACATGGTACACGCCTAGAGTCGTATAGCGTTGTGCAATCACTGCGAT

ACGTAGCATG

Index3_on_Index4
(SEQ ID NO: 11)
ACAGGTTCAGAGTTCTACAGTCCGACGATCCTGGAGTTCAGACGTGTGCT

CTTCCGATCT

Index4_on_Index3
(SEQ ID NO: 12)
CTGGAGTTCAGACGTGTGCTCTTCCGATCTACAGGTTCAGAGTTCTACAG

TCCGACGATC

Example 3

In this experiment, construction of ligation products using 4 oligo duplexes was demonstrated. This experiment was very similar to the two-part assembly described in Example 2, in that a bridge is formed between two duplexes but for two distinct pairs of duplexes, where each duplex is tethered to the surface by a short (30-mer) single-stranded section region of one of the two strands of each duplex. The difference is that one end of each bridge is cleaved leaving the indexing tether sequence bound to the surface-bound oligo (of the array). In this embodiment, the cleavage is performed by cleavage of a photocleavable linker (a PC-linker as provided by Trilink Biotechnologies) between the indexing portion and the cargo portion of the oligo, and leaving a 5'-overhanging with a phosphate group on the free end of the double stranded intermediate product. Since this happens for two distinct oligo constructs within each feature, and each has a complementary overhang, these ends are free to ligate to each other. This was achieved by two methods. In a first method, a ligase solution was loaded into the well and allowed to work for 10 minutes, then eluted before photocleavage, and the chamber was refilled with a fresh oligo solution for another 10-minute reaction. Photocleavage was performed with a 365 nm LED infra-red lamp for a 10-minute exposure. In a separate well, the same ligation solution was used throughout with exposure to the UV lamp for the intervening 10 minutes of a 30-minute ligation reaction.

For designing oligos for complex 2-part assembly, each oligo library (OLS) is produced by cleavage of 244,000 feature oligos from a full-slide array. In this case, each library was constructed to file one of three full length genes with oligos of 50, 80, 120 and 170 bp plus a read primer (23 or 25 bp) and an indexing sequence (30 bp) on a single strand of each duplex, as shown in FIG. 14, The genes contained 58 or 68 segments where each pair of adjacent segments are designed to form a construct. Although each construct is adjacent in the gene, and each has a 5' overhang at both ends, there is no immediate intent to assemble full length genes, but simply to demonstrate the capability of the current assay. Thus there were 1800 to 2100 features used to produce each oligo sequence.

The constructs were designed in a semi-random fashion in terms of which oligo lengths were to be assembled together. So, some shorter oligo duplexes were ligated to long oligo shorter. Common read primers were included within each longer oligo (indexing) sequence of each construct, but the constructs for each gene were amplified by PCR with different library prep PCR primers, with distinct read indices.

The OLS library oligos as constructed do not have phosphates on their 5'-ends, so they were be kinased, which was done as with the individual oligos as described above. The hybridization and ligation assays were also performed as with the discrete oligos, with approximately half the product (5 pmoles) of each OLS library in a different well. The fourth well contained a mixture of three libraries but with only 1 pmole of each library. Each indexing array has 100, 200 and 400 features for each index oligos, with the majority of indexing oligos having 100 features. The ligation was performed at 16° C. with an excess of T4-ligase enzyme with a total of 12 uL into a total volume of 700 uL as used for all four wells, where each well used between 120-150 uL of ligase solution.

Each library of assembled constructs was eluted from each array at 3 temperatures (50°, 60° and 70° C.) as described for the discrete oligos, and the 60° elution was used in the subsequent sequencing assay. Each library was amplified with sequencing adapters with 10 cycles of PCR using Herculase™ buffer from Agilent Technologies, according to manufacturer's specifications. The amplified libraries were purified using SPRI beads to clean up small DNA, such as primers. The cleaned up amplification products for each individual library is shown in FIG. 15. The fourth well with the mixture of libraries did not indicate significant products for 10 PCR cycles, although it did with 15 cycles. The cleaned up amplification products were run on an Illumina MiSeq sequencer using a 75 bp paired-end read kit.

The test of specificity is how many cross-ligations occur between unintended constructs compared with how many intended constructs were detected. This was assessed by using paired-end sequencing, where the all reads are mapped by alignment to the sequence of the complete gene. For a correct construct read 1 aligns to the first segment of each construct sequence and read2 (at the other end of the PCR product) aligns to the second segment of the same intended construct sequence.

The total number paired reads that aligned to the gene EK499 was U.S. Pat. No. 7,186,818. Of these, the number of reads for which read 1 aligns to the first part of a construct, and read 2 aligns to the second part of the same targeted construct is U.S. Pat. No. 7,166,833 counts for all 34 constructs. And the sum of all read counts across different constructs is 3148 counts, meaning that only 0.04% of oligonucleotides non-specifically cross-ligated. Within this set of constructs, there exists only one pair of constructs that share a common 5-bp overhang sequence. For solution phase ligation, where all oligos are free to cross-ligate between all oligos with a common overhang, cross-ligation would be comparable to targeted ligation. But for this process, with oligos attached to solid phase specifically spatially isolate to each feature, the cross ligation was measured at only 353 counts, well below 1% of the counts of the two intended constructs at 329,734 and 207,704 counts.

FIG. 16 shows the representations of the intended constructs as the determined by read 1 and read 2 alignments. The least represented construct is the 9$^{th}$ construct with only 3108, about 25 times lower than the median of other constructs. This particular construct is one of the longest at 295 bp. FIG. 17 shows that longer constructs are substantially less represented than shorter constructs. There are several potential affects that may reduce the representations of longer constructs. First, due to the nucleotide coupling yield during synthesis, there are fewer long full length oligonucleotides than shorter oligonucleotides. For a per base coupling yield of 99.2%, this would account for a factor of 5 fewer constructs at 300 nt than at 100 nt. If there are fewer oligonucleotides hybridized to the index probes within a feature, then the density of oligos will be lower, making it more difficult for bridges to form by ligation, and reducing the yield. Finally, as the products are amplified by PCR, both during library preparation for sequencing and during sequencing, it is likely that some of the reduction is due to PCR that may be less efficient for longer amplicons than for shorter ones. The combination of these factors generally makes the production of longer constructs far less efficient than shorter constructs.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

Exemplary Embodiments

Provided herein is a method comprising:

Embodiment 1. A method for producing a ligation product, comprising; hybridizing a first double-stranded oligonucleotide and a second double-stranded oligonucleotide to a substrate comprising surface-tethered oligonucleotides; and ligating the surface-distal ends of the first and second double-stranded oligonucleotides together, thereby producing a first ligation product that is tethered to the support at both ends.

Embodiment 2. The method of embodiment 1, wherein;
(i) the first double-stranded oligonucleotide has overhangs at both ends;
(ii) the second double-stranded oligonucleotide has overhangs at both ends;
(iii) the overhangs at a first end of the first and second double-stranded oligonucleotides are ligation compatible; and
(iv) the overhangs at the second end of the first and second double-stranded oligonucleotides are complementary to a surface-tethered oligonucleotide.

Embodiment 3. The method of embodiment 2, wherein the overhangs at the first end of the first and second double-stranded oligonucleotides are in the range of 1 to 9 bases in length.

Embodiment 4. The method of embodiment 2, wherein the overhangs at the second end of the first and second double-stranded oligonucleotides are in the range of 10 to 40 bases in length.

Embodiment 5. The method of any prior embodiment, wherein the ligating also ligates the surface-proximal end of the first double-stranded oligonucleotide to a surface-tethered oligonucleotide.

Embodiment 6. The method of any prior embodiment, further comprising cleaving the surface-proximal end of the second double-stranded oligonucleotide to release one end of the first ligation product from the support.

Embodiment 7. The method of embodiment 6, wherein the second double-stranded oligonucleotide comprises a cleavable linkage, and the cleaving is done by cleaving the cleavable linkage.

Embodiment 8. The method of embodiment 7, wherein the second double-stranded oligonucleotide comprises a photocleavable or chemically cleavable linkage, the cleaving is done by exposing the ligation product to light or a chemical.

Embodiment 9. The method of embodiment 6, wherein the cleaving is done using a restriction enzyme.

Embodiment 10. The method of any of embodiments 6-9, wherein the cleaving results in production of an overhang at the end of the first ligation product.

Embodiment 11. The method of embodiment 10, further comprising ligating the overhang at the end of the first ligation product to a compatible overhang of a third double-stranded oligonucleotide that is tethered to the support, or a ligation product containing the third double-stranded oligonucleotide, thereby producing a second ligation product that is tethered to the solid support at both ends.

Embodiment 12. The method of embodiment 11, wherein the overhang at the end of the first ligation product is ligated to a third double-stranded oligonucleotide, wherein the third double-stranded oligonucleotide has a first end that is tethered to the support and a second end that has an overhang that is ligation compatible with the overhang at the end of the first ligation product.

Embodiment 13. The method of embodiment 11, wherein the overhang at the end of the first ligation product is ligated to a third ligation product, wherein the third ligation product comprises the third double-stranded oligonucleotide, and wherein the ligation product has a first end that is tethered to the support and a second end that has an overhang that is ligation compatible with the overhang at the end of the first ligation product.

Embodiment 14. The method of any of embodiments 11-13, further comprising cleaving an end of the second ligation product, thereby releasing one end of the ligation product from the support.

Embodiment 15. The method of any of embodiments 11-14, further comprising amplifying the second ligation product.

Embodiment 16. The method of any prior embodiment, wherein the support is planar.

Embodiment 17. The method of any prior embodiment, wherein the hybridizing is done at a temperature that does not denature the first and second double-stranded oligonucleotides.

Embodiment 18. The method of embodiment 17, wherein the hybridizing is done at high stringency at a temperature of 55° C. to 70° C., or an equivalent thereof.

Embodiment 19. The method of any prior embodiment, wherein the substrate comprises multiple populations of surface-tethered oligonucleotides, wherein each population of surface-tethered oligonucleotides occupies a spatially distinct region on the support.

Embodiment 20. The method of embodiment 19, wherein the substrate comprises at least 2, at least 10, at least 100, at least 1000 or at least 10,000 populations of surface-tethered oligonucleotides, wherein each population of surface-tethered oligonucleotides occupies a spatially distinct region on the support. In these embodiments, the regions occupied by the surface-tethered oligonucleotides may be in the form of an array.

Embodiment 21. The method of any of embodiments 6-20, further comprising eluting the first ligation product in at least two elutions, wherein a first of the elutions is at a lower temperature than a second of the elutions.

Embodiment 22. The method of any of the foregoing embodiments, wherein one or more of the various treatments (for example, hybridizing and/or ligating, and/or cleaving) are done in droplets on the surface of the support.

What is claimed is:

1. A method for producing a ligation product on a support, comprising:
   providing the support, which comprises a surface and surface-tethered oligonucleotides;
   hybridizing a first double-stranded oligonucleotide and a second double-stranded oligonucleotide to the surface-tethered oligonucleotides, and as a result the hybridized first and second double stranded oligonucleotides comprise surface-proximal ends and surface-distal ends, wherein the surface-proximal ends are tethered to the support through the surface-tethered oligonucleotides; and
   ligating the surface-distal ends of the first and second double-stranded oligonucleotides together, thereby producing a first double-stranded ligation product that is tethered to the support at both ends.

2. The method of claim 1, wherein:
   (i) the first double-stranded oligonucleotide has overhangs at both ends;
   (ii) the second double-stranded oligonucleotide has overhangs at both ends;
   (iii) the overhangs at a first end of the first and second double-stranded oligonucleotides are ligation compatible; and
   (iv) the overhangs at the second end of the first and second double-stranded oligonucleotides are complementary to a surface-tethered oligonucleotide.

3. The method of claim 2, wherein the overhangs at the first end of the first and second double-stranded oligonucleotides are in the range of 1 to 9 bases in length.

4. The method of claim 2, wherein the overhangs at the second end of the first and second double-stranded oligonucleotides are in the range of 10 to 40 bases in length.

5. The method of claim 1, wherein the ligating also ligates the surface-proximal end of the first double-stranded oligonucleotide to a surface-tethered oligonucleotide.

6. The method of claim 1, further comprising cleaving the surface-proximal end of the second double-stranded oligonucleotide to release one end of the first ligation product from the support.

7. The method of claim 6, wherein the second double-stranded oligonucleotide comprises a cleavable linkage, and the cleaving is done by cleaving the cleavable linkage.

8. The method of claim 7, wherein the second double-stranded oligonucleotide comprises a photocleavable or chemically cleavable linkage, the cleaving is done by exposing the ligation product to light or a chemical.

9. The method of claim 6, wherein the cleaving is done using a restriction enzyme.

10. The method of claim 6, wherein the cleaving results in production of an overhang at the end of the first ligation product.

11. The method of claim 10, further comprising ligating the overhang at the end of the first ligation product to a compatible overhang of a third double-stranded oligonucleotide that is tethered to the support, or a ligation product containing the third double-stranded oligonucleotide, thereby producing a second ligation product that is tethered to the support at both ends.

12. The method of claim 11, wherein the overhang at the end of the first ligation product is ligated to a third double-stranded oligonucleotide, wherein the third double-stranded oligonucleotide has a first end that is tethered to the support and a second end that has an overhang that is ligation compatible with the overhang at the end of the first ligation product.

13. The method of claim 11, wherein the overhang at the end of the first ligation product is ligated to a third ligation product, wherein the third ligation product comprises the third double-stranded oligonucleotide, and wherein the ligation product has a first end that is tethered to the support and a second end that has an overhang that is ligation compatible with the overhang at the end of the first ligation product.

14. The method of claim 11, further comprising cleaving an end of the second ligation product, thereby releasing one end of the ligation product from the support.

15. The method of claim 11, further comprising amplifying the second ligation product.

16. The method of claim 6, further comprising eluting the first ligation product in at least two elutions, wherein a first of the elutions is at a lower temperature than a second of the elutions.

17. The method of claim 1, wherein the support is planar.

18. The method of claim 1, wherein the hybridizing is done at a temperature that does not denature the first and second double-stranded oligonucleotides.

19. The method of claim 18, wherein the hybridizing is done at high stringency at a temperature of 45° C. to 70° C.

20. The method of claim 1, wherein the support comprises multiple populations of surface-tethered oligonucleotides, wherein each population of surface-tethered oligonucleotides occupies a spatially distinct region on the support.

21. The method of claim 20, wherein the support comprises at least 100 populations of surface-tethered oligonucleotides, wherein each population of surface-tethered oligonucleotides occupies a spatially distinct region on the support.

22. The method of claim 1, wherein the first double-stranded oligonucleotide and the second double-stranded oligonucleotide are hybridized to surface-tethered oligonucleotides at a common feature of the support, wherein both the first double-stranded oligonucleotide and the second double-stranded oligonucleotide comprise a common indexing sequence capable of binding the surface-tethered oligonucleotides at the common feature.

* * * * *